(12) United States Patent
Detti

(10) Patent No.: US 11,535,676 B2
(45) Date of Patent: Dec. 27, 2022

(54) ANTI-MULLERIAN HORMONE RECEPTOR BINDING PEPTIDES

(71) Applicant: Laura Detti, Gates Mills, OH (US)

(72) Inventor: Laura Detti, Gates Mills, OH (US)

( * ) Notice: Subject to any disclaimer, the term of this patent is extended or adjusted under 35 U.S.C. 154(b) by 0 days.

(21) Appl. No.: 17/456,205

(22) Filed: Nov. 23, 2021

(65) Prior Publication Data

US 2022/0073633 A1 Mar. 10, 2022

Related U.S. Application Data

(63) Continuation of application No. PCT/US2020/035472, filed on May 30, 2020.

(60) Provisional application No. 62/855,427, filed on May 31, 2019.

(51) Int. Cl.
  *C07K 16/28* (2006.01)
  *A61P 43/00* (2006.01)
  *A61K 39/00* (2006.01)

(52) U.S. Cl.
  CPC .......... *C07K 16/2869* (2013.01); *A61P 43/00* (2018.01); *A61K 2039/505* (2013.01)

(58) Field of Classification Search
  CPC .................................................. C07K 16/2869
  See application file for complete search history.

(56) References Cited

U.S. PATENT DOCUMENTS

| | | |
|---|---|---|
| 2016/0039898 A1 | 2/2016 | Donahoe et al. |
| 2017/0218091 A1 | 8/2017 | Ambrosi |
| 2017/0239333 A1 | 8/2017 | Meirow et al. |
| 2017/0258842 A1 | 9/2017 | Al-Hendy |
| 2018/0236034 A1 | 8/2018 | Sen |

FOREIGN PATENT DOCUMENTS

WO 2018112168 A1 6/2018

OTHER PUBLICATIONS

ClustalW Alignment for SEQ ID Nos. 1-20. NCBI. Obtained Jun. 17, 2022. (Year: 2022).*
PCT/US2020/035472, International Search Report and Written Opinion, dated Sep. 21, 2020 (13 pages).

* cited by examiner

*Primary Examiner* — Elly-Gerald Stoica
(74) *Attorney, Agent, or Firm* — FisherBroyles, LLP; Jason M. Pass

(57) ABSTRACT

Disclosed are compositions and methods including Anti-Müllerian Hormone (AMH) receptor binding peptides. The AMH receptor binding peptides can be used, for example, to modify the activity of the AMH receptor. For example, the AMH receptor binding peptides can activate the AMH receptor, such as the AMH receptor 2, thereby mimicking the function of AMH. In other examples, the AMH receptor binding peptides function as AMH receptor antagonists, thereby interfering with the function of endogenous AMH. By modifying the activity of the AMH receptor, the peptides have multiple applications, including for example modification of treatment of precocious puberty in females, delay of natural menopause, preservation of ovarian follicular reserve, contraception, fertility preservation after ovarian cortex transplant, treatment of endometriosis, treatment of cancer and/or cancer prevention, and treatment of polycystic ovary syndrome (PCOS).

20 Claims, 6 Drawing Sheets

Specification includes a Sequence Listing.

ANTI-MULLERIAN HORMONE RECEPTOR BINDING PEPTIDES

CROSS-REFERENCE TO RELATED APPLICATIONS

This application is a continuation of International Pat. App. No. PCT/US2020/035472, filed May 30, 2020, which claims priority benefit to U.S. Provisional App. No. 62/855,427, filed May 31, 2019, both of which are titled "ANTI-MULLERIAN HORMONE RECEPTOR BINDING PEPTIDES & USES THEREOF" and both of which are hereby fully incorporated herein by reference in their entirety.

SEQUENCE LISTING

The instant application contains a Sequence Listing which has been submitted electronically in ASCII format and is hereby incorporated by reference in its entirety. Said ASCII copy, created on Nov. 22, 2021, is named 14117-001US1_ST5.txt and is 8,719 bytes in size.

FIELD OF THE INVENTION

The present invention relates generally to peptides that bind Anti-Mullerian Hormone (AMH) receptors, and more particularly to peptides can modify physiological and pathophysiological functions in tissues/organs that include AMH receptors.

BACKGROUND OF THE INVENTION

Anti-Müllerian hormone (AMH), also called Müllerian inhibiting substance (MIS) or Müllerian inhibiting factor (MIF), is a member of the transforming growth factor β (TGFβ) superfamily of peptide growth and differentiation factors. During fetal sex differentiation, AMH expression is restricted in the male to the Sertoli cells of fetal and postnatal testis. When present, AMH induces degeneration of the Müllerian ducts, which otherwise form the anlagen of the uterus, the oviducts, and the upper part of the vagina. The Wolffian duct then persists—in the presence of AMH—resulting in the urogenital structures that include the epididymis, vas deferens, and seminal vesicles of the male. In the postnatal male, AMH production persists in the Sertoli cells, though little is known about the action of AMH in the male following birth. During female fetal development, minimal ovarian AMH production occurs.

In the postnatal female, AMH is produced exclusively in the ovary by growing follicles, with AMH mRNA expression first being detected in ovarian granulosa cells from postnatal day 3 onwards. Thereafter, the follicles remain as primordial follicles in the prepubescent female, each primordial follicle including an oocyte that is surrounded by a single layer of squamous follicular cells. But starting at puberty—and during each estrous cycle thereafter—a subset of the primordial follicles transition to primary follicles, a process that is under hormonal regulation of paracrine hormones. These hormones include, for example, AMH and the pituitary hormones follicle stimulating hormone (FSH) and luteinizing hormone (LH). FSH is the main activator during the follicular phase, causing follicular growth and development after binding to its receptor FSH-R.

Progression of at least one of the primary follicles to a dominant follicle is regulated by AMH. AMH is secreted by the granulosa cells, with its production starting at the stage of primary follicles, soon after the columnar differentiation from the flat granulosa cells of primordial follicles. Production of AMH is maximum in secondary follicles, gradually decreases in early tertiary follicles, and is nil in antral tertiary follicles when the follicles are primarily under FSH control. The primary action of AMH is inhibitory on other granulosa cells, where it precludes primordial follicles from progressing to primary follicles, thereby preserving the primary follicle pool. AMH also aids in the selection of the dominant follicle by reducing expression of the FSH receptor in the granulosa cells. As noted above, for example, binding of FSH to its cognate receptor triggers follicular growth and development. Hence, by acting to reduce the expression of the FSH receptor, AMH secretion by a primary follicle that is destined to become the dominant follicle acts to reduce FSH-mediated growth and development of other follicles, thereby preventing multiple dominant follicles and multiple oocyte ovulation. A pathophysiological example of this inhibitory function is polycystic ovary syndrome: women with this condition have elevated AMH levels and their serum AMH concentration correlates with their anovulatory pattern [16].

Notably, the function of AMH to preclude the transition of primordial follicles to primary follicles is crucial in preserving the ovarian follicle reserve. This is because once a primordial follicle progresses to a primary follicle, that primary follicle is destined to differentiate into a secondary and tertiary follicle and ultimately undergo apoptosis within 120 days. Hence, by decreasing the number of primordial follicles that transition to primary follicles, the number of primordial follicles is preserved. Nonetheless, it is estimated that—even with normal levels of AMH—about 1,000 primordial follicles are lost to apoptosis per each menstrual cycle during a female's life.

To exert its physiological functions, the action of AMH is mediated by several receptors, the best known of which is Anti-Müllerian hormone Receptor 2 (often abbreviated AMH-R2, $AMHR_2$, AMHRII, or the like). By binding to AMH-R2 on granulosa cells, AMH also influences other transcription factors and regulates gene transcription of other cytokines. Encoded by chromosome 12q13.13, AMH-R2 is a transmembrane serine/threonine kinase receptor which activates SMAD transcriptional regulators. In the ovary, AMHR2 is localized on granulosa and thecal cells, while it is not found on the oocyte.

Because of the role AMH plays in both prenatal development and postnatal endocrine physiology, the ability to modulate the activity of the AMH receptor has vast therapeutic implications. For example, administration of recombinant AMH has been shown to preserve the primordial follicle pool during chemotherapy. And in mice studies, administration of recombinant AMH has been shown to prevent post-transplant follicular tissue activation [9]. Modulation of the AMH receptor also has implications in the field of oncology, which has focused on the AMH signal transduction pathway—with the goal of identifying new approaches for therapeutic intervention and diagnostics.

While much is known about AMH and its receptor, however, what are needed are compositions, such as AMH receptor agonists, that can modify the activity of one or more of the AMH receptors. Also needed are methods for regulating the one or more AMH receptors, such as methods of stimulating and/or inhibiting AMH receptors. Indeed, because of the many functions of AMH, such methods and compositions could be used in the modulation of many physiological and pathophysiological conditions related to the AMH/AMH receptor pathway.

SUMMARY

In certain example aspects described herein, provided is an anti-Mullerian hormone (AMH) receptor binding peptide or functional fragment thereof, the peptide or fragment thereof including an amino acid sequence at least 85%, 90%, 95%, 98% or more identical to any one of the amino acid sequences set forth as SEQ ID NOS: 1-20. For example, the AMH receptor binding peptide or fragment thereof can be an AMH-$R_2$ receptor binding peptide having at least 85%, 90%, 95%, 98% or more identity to one or more of the amino acid sequences set forth as SEQ ID NO: 1-20.

In certain example aspects, the AMH receptor binding peptide or fragment thereof can include one or more D-form amino acids, such as three D-amino acids. In certain example aspects, the AMH receptor binding peptide or fragment thereof is an AMH receptor agonist, and thus can be used to mimic the effects of AMH. In certain example embodiments, the AMH receptor binding peptide or fragment thereof is an AMH receptor antagonist. In certain example aspects, the action of the AMH receptor binding peptide or fragment thereof is cell and/or tissue specific.

In certain examples aspects, provided is a composition, the composition including one or more AMH receptor binding peptides or functional fragment thereof, the peptides or fragments thereof including an amino acid sequence that is at least 85%, 90%, 95%, 98% or more identical to any one of the sequences set forth as SEQ ID NOS: 1-20.

In certain example aspects, provided are methods of use and/or treatment that rely on activation of the anti-Mullerian hormone receptor by one or more the AMH receptor binding peptides or fragments thereof described herein. For example, in certain aspects provided is a method for activating an anti-Mullerian hormone (AMH) receptor in a subject, the method including administering to the subject an effective amount of one or more of the AMH receptor binding peptides or fragments thereof described herein. When administered, for example, the one or more AMH receptor binding peptides or fragments thereof can inhibit precocious puberty, such as central precocious puberty arising from an intracranial mass, or a precocious puberty arising from McCune Albright syndrome (peripheral).

In certain example aspects, one or more of the AMH receptor binding peptides or fragments thereof described herein can be administered to delay menopause, preserve ovarian follicle reserves, prevent ovulation, treat endometrioses, and/or prolong the function of a transplanted ovarian cortex. In certain example aspects, the AMH receptor binding peptides or fragments thereof can be administered along with one or more hormones, such as estrogen and/or progesterone. In certain example aspects, one or more of the AMH receptor binding peptides or fragments thereof can be administered to increase or decrease sperm count.

In certain example aspects, provided is a method for reducing cell proliferation in a subject, the method including administering to the subject an effective amount the AMH receptor binding peptide or fragment thereof of one or more of the AMH receptor binding peptides described herein. For example, the cell can be a cancer cell such as ovarian cancer cell or breast cancer cell. In certain example aspects, the cell is a melanoma cell, such as an ocular melanoma cell. In still other example aspects, the cancer cell is a breast cancer cell. Hence, in certain examples embodiments, provided are methods of treating cancer in a subject, the method including administration to a subject an effective amount of one or more the AMH receptor binding peptides or fragments thereof described herein. The cancer can be, for example, ovarian cancer, breast cancer, or a melanoma.

In certain example aspects, provided is a method for treating precocious puberty in a subject, the method including administering to a subject an effective amount of one or more of the AMH receptor binding peptides or fragments thereof described herein. The precocious puberty can be a central precocious puberty, a precocious puberty arising from McCune Albright syndrome, or a precocious puberty arising from an intracranial mass.

In certain example aspects, provided is a method of treating or delaying menopause in a subject, the method including administering to a subject an effective amount of one or more of the AMH receptor binding peptides or fragments thereof described herein. In certain example aspects, provided is a method of treating infertility in a subject, the method including administering to a subject an effective amount of one or more of the AMH receptor binding peptides or fragments thereof described herein. In certain example aspects, such methods of treatment can include co-administering estrogen and/or progesterone to the subject.

In certain example aspects, such as when the AMH receptor binding peptide functions as an antagonist, provided is a method for promoting the recruitment of primordial follicles into the pool of growing follicles in a subject, the method including administering to the subject one or more of the AMH receptor binding peptides or fragments thereof described herein. In further example aspects, provided is a method for treating polycystic ovary syndrome (PCOS), the method including administering to the subject one or more of the AMH receptor binding peptides or fragments thereof described herein.

These and other aspects, objects, features and advantages of the example embodiments will become apparent to those having ordinary skill in the art upon consideration of the following detailed description of illustrated example embodiments.

DETAILED DESCRIPTION OF THE EXAMPLE EMBODIMENTS

Figure 1A:
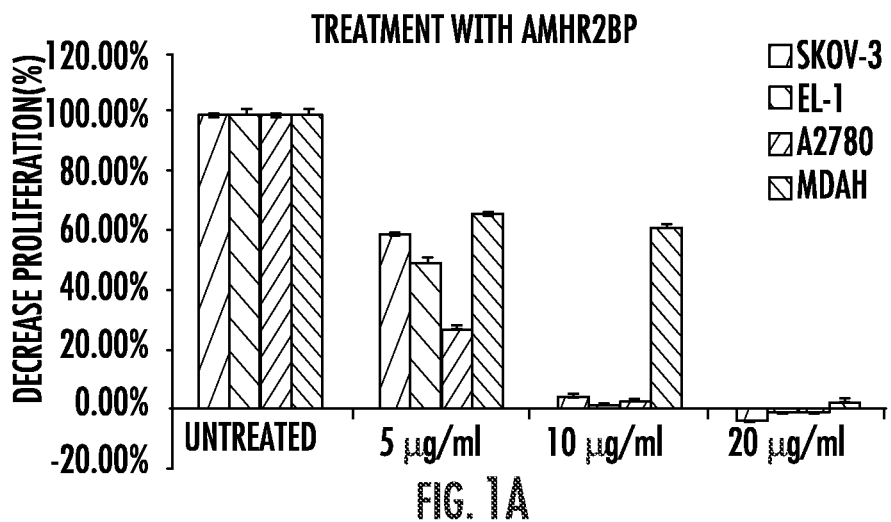
FIG. 1A is a graph showing the effects of the Anti-Müllerian hormone Receptor 2 binding peptide AMHR2BP (SEQ ID NO: 1) on cellular replication in various cancer lines, in accordance with certain example embodiments. As shown, treatment of SKOV-3 (ovarian serous cystadenocarcinoma), EL-1 (epithelial ovarian cancer), A2780 (endometroid ovarian cancer), and MDAH (endometroid ovarian cancer) cells with 5 µg/ml, 10 µg/ml, and 20 µg/ml of AMHR2BP (SEQ ID NO: 1) resulted in decreased cell proliferation as compared to untreated, control cells.

The following description and drawings are illustrative and are not to be construed as limiting. Numerous specific details are described to provide a thorough understanding of the disclosure. In certain instances, however, well-known or conventional details are not described to avoid obscuring the description. References to one or an embodiment in the present disclosure can be, but not necessarily, are references to the same embodiment; and, such references mean at least one of the embodiments.

Terminology

Unless otherwise noted, technical terms are used according to conventional usage. Definitions of common terms in molecular biology may be found in Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); and Robert A. Meyers (ed.), Molecular Biology and Biotechnology: a Comprehensive Desk Reference, published by VCH Publishers, Inc., 1995 (ISBN 9780471185710) and other similar references. As used herein, the singular forms "a," "an," and "the," refer to both the singular as well as plural, unless the context clearly indicates otherwise. The abbreviation, "e.g." is derived from the Latin exempli gratia and is used herein to indicate a non-limiting example. Thus, the abbreviation "e.g." is synonymous with the term "for example." As used herein, the term "comprises" means "includes." All publications, patent applications, patents, and other references mentioned herein are expressly incorporated herein by reference in their entirety.

It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. In case of conflict, the present specification, including explanations of terms, will control. In addition, the materials, methods, and examples are illustrative only and not intended to be limiting. To facilitate review of the various example embodiments of this disclosure, the explanations of specific terms are provided below.

An "anti-Müllerian hormone receptor binding peptide" or "AMH receptor binding peptide" is a peptide that binds to the anti-Müllerian hormone receptor, such as the AMH-I receptor and/or AMHII receptor, such as any of the peptides identified in Table 1 or derivatives or modified versions thereof. Such AMH receptor binding peptides also include functional fragments of the AMH receptor binding peptides. And as used throughout this disclosure, it is understood that any reference to "AMH receptor binding peptide" or the like also includes such functional fragments thereof, whether or not such functional fragment is used along with the phrase "AMH receptor binding peptide" or the like. For example, and unless specified otherwise, each reference to one or more the SEQ ID NOS:1-20 described herein includes a functional fragment thereof. Further, the use or reference to a fragment as being "functional" refers to the fact that the fragment can confer function, such as when administered to a subject. For example, the functional aspect can be an agonistic effect, such as mimicking the function of AMH, or an antagonistic effect, such as inhibiting the effects of AMH and/or blocking the AMH receptor.

"Administration" or "administering" refers to the introduction of a composition into a subject by a chosen route. For example, if the chosen route is intravenous, the composition is administered by introducing the composition into a vein of the subject. In some examples, the AMH peptides disclosed herein are administered to a subject. Similarly, the term "co-administration" or the like mean administering two or more compositions to a subject, either simultaneously or serially, such as in a single dose or multiple doses provided at different times.

"Carrier" refers to conventional pharmaceutically acceptable carriers. *Remington's Pharmaceutical Sciences*, by E. W. Martin, Mack Publishing Co., Easton, Pa., 19$^{th}$ Edition (1995), for example, describes compositions and formulations suitable for pharmaceutical delivery of the peptides disclosed herein. In general, the nature of the carrier will depend on the particular mode of administration being employed. For instance, parenteral formulations usually include injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional nontoxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

"Controlled release" or "controlled release formulation" refers to a formulation designed to consistently release a predetermined, therapeutically effective amount of drug or other active agent such as a polypeptide or a synthetic compound below toxic levels over an extended period of time, with the result being a reduction in the number of treatments necessary to achieve the desired therapeutic effect. Preferably the amount of the drug or active agent in the implantable formulations according to embodiments of the present invention establish a therapeutically effective plasma concentration of the drug over a period of 1 month or longer. As an example, a controlled formulation would decrease the number of treatments necessary to achieve the desired effect in terms of decreased estradiol levels or improvement in symptoms associated with precocious puberty. A controlled release formulation can, for example, achieve a desired pharmacokinetic profile in a subject, preferably commencement of the release of the active agent substantially immediately after placement in a delivery environment, followed by consistent, sustained, preferably zero-order or near zero-order release of the active agent.

Example carriers include excipients or stabilizers that are nontoxic to the cell, tissue, mammal, or subject being exposed thereto at the dosages and concentrations employed. Often the pharmaceutically acceptable carrier is an aqueous pH buffered solution. Examples of pharmaceutically acceptable carriers also include, without limitation, buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; saltforming counterions such as sodium; and/or nonionic surfactants such as Tween®, polyethylene glycol (PEG), and Pluronics®. As used herein, a chimeric antibody refers to an antibody which includes sequences derived from two different antibodies, which typically are of different species. Most typically, chimeric antibodies include human and murine antibody fragments, generally human constant and murine variable regions.

The term "cancer" is used herein in its broadest sense and refers to a family of diseases characterized by uncontrolled cell growth. The term includes, for example, adrenocortical carcinoma, anal cancer, bladder cancer, brain stem glioma, brain tumor, cerebellar astrocytoma, cerebral astrocytoma, ependymoma, medulloblastoma, supratentorial primitive neuroectodermal, pineal tumors, hypothalamic glioma, breast cancer, carcinoid tumor, carcinoma, cervical cancer, colon cancer, endometrial cancer, esophageal cancer, extrahepatic bile duct cancer, ewings family of tumors, extracranial germ cell tumor, eye cancer, intraocular melanoma, gallbladder cancer, gastric cancer, germ cell tumor, extragonadal germ cell tumor, gestational trophoblastic tumor, head and neck cancer, hypopharyngeal cancer, islet cell carcinoma, laryngeal cancer, acute lymphoblastic leukemia, oral cavity cancer, liver cancer, lung cancer, small cell lymphoma, AIDS-related lymphoma, central nervous system (primary) lymphoma, cutaneous T-cell lymphoma, hodgkin's disease, non-hodgkin's disease, malignant mesothelioma, melanoma, merkel cell carcinoma, metastatic squamous carcinoma, multiple myeloma, plasma cell neoplasms, mycosis fungoides, myelodysplastic syndrome, myeloproliferative disorders, nasopharyngeal cancer, neuroblastoma, oropharyngeal cancer, osteosarcoma, ovarian epithelial cancer, ovarian germ cell tumor, ovarian low malignant potential tumor, pancreatic cancer, exocrine pancreatic cancer, paranasal sinus and nasal cavity cancer, parathyroid cancer, pheochromocytoma cancer, pituitary cancer, plasma cell neoplasm, rhabdomyosarcoma, rectal cancer, renal cell cancer, salivary gland cancer, sezary syndrome, kaposi's sarcoma, skin cancer, small intestine cancer, soft tissue sarcoma, thymoma, malignant, thyroid cancer, urethral cancer, uterine cancer, sarcoma, unusual cancer of childhood, vaginal cancer, vulvar cancer, or wilms' tumor.

"DNA" (deoxyribonucleic acid) refers to a long chain polymer which constitutes the genetic material of most living organisms (some viruses have genes composed of ribonucleic acid (RNA)). The repeating units in DNA polymers are four different nucleotides, each of which contains one of the four bases, adenine, guanine, cytosine and thymine bound to a deoxyribose sugar to which a phosphate group is attached. Triplets of nucleotides (referred to as codons) code for each amino acid in a polypeptide. The term codon is also used for the corresponding (and complementary) sequence of three nucleotides in the mRNA that is transcribed from the DNA.

"Effective amount" or "suitable amount" or "therapeutically effective amount" refers to an amount of a substance sufficient to affect the beneficial or desired clinical or biochemical results. An effective amount can be administered one or more times. For example, an effective amount of an AMH receptor binding peptide as described herein is an amount that is sufficient to bind an AMH receptor and exert an effect, such as modifying the activity of the AMH receptor. For example, binding of an effective amount of an AMH receptor binding peptide as described herein may stimulate the receptor. Or, in certain example embodiments an effective amount of an AMH receptor binding peptide may antagonize the AMH receptor, such as by competing with endogenous AMH for receptor binding. As an example, a peptide may be effective, for example, when parenterally administered in amounts above about 1 µg per kg of body weight to about 30 mg/kg body weight.

As those skilled in the art will appreciate, an effective amount of a therapeutic compound or composition necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the subject being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. One of ordinary skill in the art would be able to study the relevant factors and make the determination regarding the effective amount of the therapeutic compound without undue experimentation. In certain example embodiments, a medical doctor, e.g., physician or veterinarian, having ordinary skill in the art may readily determine and prescribe the effective amount of the pharmaceutical composition required. For example, the physician or veterinarian could start doses of the compounds or compositions of the invention employed in the pharmaceutical composition at levels lower than that required in order to achieve the desired therapeutic effect and gradually increase the dosage until the desired effect is achieved.

The terms "inhibit" or "inhibits," as used herein, refer to reducing or removing by a measurable degree. For example, the administration of one or more the AMH receptor binding peptide as described herein may inhibit cell replication, meaning that the administration reduces the cell replication by a measurable degree. Such a reduction, for example, may be small inhibition, such as about 5%, 10%, or 15% reduction. In other examples, the inhibition may be greater, such as about 20%, 25%, 30%, 35%, 40%, 45%, 50%, 55%, 60%, 65%, 70%, 75%, 80% or more reduction. In other example embodiments, the inhibition can be a complete inhibition, such as a 100% reduction in an effect or outcome.

"Label" refers to a detectable compound or composition that is conjugated directly or indirectly to another molecule to facilitate detection of that molecule. Specific, non-limiting examples of labels include fluorescent tags, chemiluminescent tags, haptens, enzymatic linkages, and radioactive isotopes.

The phrase "in combination with" as used herein includes all forms of combined use, including simultaneous or subsequent administration, by the same or a different medicament, by the same or a different route of administration.

"Operably linked" refers to a first nucleic acid sequence that is connected to a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

The term "peptide" refers generally to any peptide or peptidomimetic structure comprising or consisting of two or more amino acids, including chemical modifications and derivatives of amino acids. A "polypeptide" refers to a polymer in which the monomers are amino acid residues that are joined together through amide bonds. When the amino acids are alpha-amino acids, either the L-optical isomer or the D-optical isomer can be used, the L-isomers being preferred. The terms "polypeptide" or "protein" as used herein is intended to encompass any amino acid sequence and include modified sequences such as glycoproteins. The term "polypeptide" is specifically intended to cover naturally occurring proteins, as well as those that are recombinantly or synthetically produced. Likewise, the term "protein" refers to a biological molecule encoded by a gene and comprised of amino acids. When used herein, a "peptide" also includes functional fragments of the peptide. For example, administration of an effective amount of an AMH receptor binding peptide includes the administration of a functional fragment of the AMH receptor binding peptide.

"Pharmaceutical composition" or "pharmaceutical gent" refers to a chemical compound or composition capable of inducing a desired therapeutic or prophylactic effect when properly administered to a subject or a cell. For example, a pharmaceutical agent may include a peptide as described herein, the administration of which results in modification of the activity of an AMH receptor, such as activation of the receptor.

"Purified" or "isolated" molecule refers to biological or synthetic molecules that are removed from their natural environment and are isolated or separated and are free from other components with which they are naturally associated. The term "purified" does not require absolute purity; rather, it is intended as a relative term. Thus, for example, a purified or "substantially pure" protein preparation is one in which the protein referred to is more pure than the protein in its natural environment within a cell or within a production reaction chamber (as appropriate).

The term "specifically binds" refers to a non-random binding reaction between two molecules, for example between a peptide of the present invention and an AMH receptor. The term "specifically binds" may be used interchangeably with "selectively targets" or "selectively associates."

The term "selectively targets" or "selectively associates" with reference to AMH receptors, refers to, for example, the selective localization or binding of the peptide to the AMH receptor. For example, an AMH receptor binding peptide as described herein can be said to selectively target the AHH receptor, thereby modifying the activity of the receptor.

"Sequence identity" refers to the similarity between two nucleic acid sequences, or two amino acid sequences, and is expressed in terms of the similarity between the sequences, otherwise referred to as sequence identity. Sequence identity is frequently measured in terms of percentage identity (or similarity or homology); the higher the percentage, the more similar the two sequences are.

Methods of alignment of sequences for comparison are well known in the art. Various programs and alignment algorithms are described in: Smith & Waterman *Adv. Appl. Math.* 2: 482, 1981; Needleman & Wunsch *J. Mol. Biol.* 48: 443, 1970; Pearson & Lipman *Proc. Natl. Acad. Sci. USA* 85: 2444, 1988; Higgins & Sharp *Gene* 73: 237-244, 1988; Higgins & Sharp *CABIOS* 5: 151-153, 1989; Corpet et al. Nuc. Acids Res. 16, 10881-90, 1988; Huang et al. *Computer Appls. In the Biosciences* 8, 155-65, 1992; and Pearson et al. *Meth. Mol. Bio.* 24, 307-31, 1994. Altschul et al. (*J. Mol. Biol.* 215:403-410, 1990), presents a detailed consideration of sequence alignment methods and homology calculations. The NCBI Basic Local Alignment Search Tool (BLAST) (Altschul et al. *J. Mol. Biol.* 215:403-410, 1990) is available from several sources, including the National Center for Biotechnology Information (NCBI, Bethesda, Md.) and on the Internet, for use in connection with the sequence analysis programs blastp, blastn, blastx, tblastn and tblastx.

A "stable" or "stabilized" formulation is one in which the protein therein essentially retains its physical and/or chemical stability upon storage. Stability can be measured at a selected temperature for a selected time period. Preferably, the formulation is stable at room temperature (30° C.) or at 40° C. for at least 1 month and/or stable at about 2-8° C. for at least 1 year and preferably for at least 2 years. For example, the extent of aggregation during storage can be used as an indicator of protein stability. Thus, a "stable" formulation may be one wherein less than about 10% and preferably less than about 5% of the protein is present as an aggregate in the formulation. Various analytical techniques for measuring protein stability are available in the art and are reviewed, for example, in *Peptide and Protein Drug Delivery*, 247-301, Vincent Lee Ed., Marcel Dekker, Inc., New York, N.Y., Pubs. (1991) and Jones, A. Adv. Drug Delivery Rev. 10: 29-90 (1993).

A "subject" refers to a vertebrate animal. The vertebrate may be a mammal, for example, such as a human. The subject may be a human "patient." A subject may be a patient suffering from or suspected of suffering from a disease or condition and may be in need of treatment or diagnosis or may be in need of monitoring for the progression of the disease or condition. The patient may also be in on a treatment therapy that needs to be monitored for efficacy. In some example embodiments, a subject includes a subject suffering from one or more physiological or pathophysiological conditions modulated by AMH and/or an AMH receptor. In certain example, cells from a subject, whether in vitro or in situ, may be amenable to the methods described herein.

The terms "treating" or "treatment" refer to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. A "prophylactic" treatment is a treatment administered to a subject who does not exhibit signs of a disease or exhibits only early signs for the purpose of decreasing the risk of developing pathology. For example, any one or more of the peptides described herein can be administered prophylactically to prevent a disease or condition, such as delaying menopause.

A "vector" refers to a nucleic acid molecule as introduced into a host cell, thereby producing a transformed host cell. Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant DNA vectors having at least some nucleic acid sequences derived from one or more viruses. The term vector includes plasmids, linear nucleic acid molecules, and as described throughout adenovirus vectors and adenoviruses.

AMH Receptor Binding Peptides

In certain example embodiments, provided herein are AMH receptor binding peptides or functional fragments thereof that can modify the activity of the AMH receptor. For example, the AMH receptor binding peptides can, in certain example embodiments, activate that AMH receptor, thereby triggering downstream signaling cascades consistent with AMH binding to the AMH receptor. In this regard, the AMH receptor binding peptides described herein are AMH receptor agonists. As such, when the AMH receptor binding peptides described herein are brought into contact with the AMH receptor, the AMH receptor binding peptides mimic AMH and hence trigger the physiological functions that are consistent with AMH binding to the AMH receptor. In other examples embodiments, the AMH receptor binding peptides can reduce or inhibit the activity AMH receptor, thereby operating as AMH receptor antagonists. For example, the AMH receptor binding peptide or functional fragment thereof may compete with binding of endogenous AMH to the AMH receptor, thereby reducing the effects of endogenous AMH.

In certain example embodiments, the AMH receptor binding peptides or functional fragments thereof have an amino acid sequence set forth as any one of SEQ ID NOS: 1-20, as provided in Table 1 (below). In other example embodiments, the AMH receptor binding peptides have an amino acid sequence that is 80%, 85%, 90%, 95%, 97%, or 98% identical to any one of the sequences set forth as SEQ ID NOS: 1-20. In certain example embodiments, the AMH receptor binding peptides having the sequence set forth as SEQ NOS: 1-20, or the AMH receptor binding peptides having identity with any one of the sequences set forth as SEQ ID NOS:1-20 as described herein, can be AMH receptor agonists.

TABLE 1

AMH Receptor Binding Peptides

| SEQ ID NO: | Amino Acid Sequence | MW | pI | Net Charge | Ecoef | Rep 1 | Rep 2 | Average |
|---|---|---|---|---|---|---|---|---|
| 1 | VGSNAYNQFrVSGValS | 1768.95 | 8.72 | 1 | 1490 | 65535 | 65535 | 65535 |
| 2 | NGSSlQAVNrlSGVS | 1807.98 | 10.84 | 2 | 1490 | 65535 | 65535 | 65535 |
| 3 | YwGwSHAkaNQFPNrla | 2046.28 | 9.99 | 2 | 12490 | 65502 | 65465 | 65484 |
| 4 | rwGaSNkHFANaNQral | 1941.14 | 12.01 | 3 | 5500 | 65509 | 65414 | 65462 |
| 5 | DGlGSVlArkNrrDaVl | 1840.12 | 10.74 | 2 | 0 | 65431 | 65475 | 65453 |
| 6 | VGPSVAYNYrVSGValG | 1708.93 | 8.56 | 1 | 2980 | 65462 | 65391 | 65427 |
| 7 | kGGYSNAYkHNPrVlGS | 1848.05 | 10 | 3 | 2980 | 65521 | 65329 | 65425 |
| 8 | wHGwSGANlFPYrSGVS | 1921.1 | 8.75 | 1 | 12490 | 65158 | 65511 | 65335 |
| 9 | VGwSFAPNGYrlSGVlG | 1780.02 | 8.72 | 1 | 6990 | 65176 | 65153 | 65165 |
| 10 | rGrSQAYNErSGValSG | 1807.94 | 10.74 | 2 | 1490 | 63931 | 65250 | 64591 |
| 11 | GSwSGAHNFrkSGVlSG | 1746.9 | 11 | 2 | 5500 | 65128 | 63787 | 64458 |
| 12 | GlQwSFANGQwrGalSG | 1835.01 | 9.75 | 1 | 11000 | 64623 | 62943 | 63783 |
| 13 | rGSYSNlFANSGErVGV | 1812.96 | 8.75 | 1 | 1490 | 63996 | 63551 | 63774 |
| 14 | FNGPSArNFYrHDVaVS | 1937.1 | 8.75 | 1 | 1490 | 65284 | 58385 | 61835 |
| 15 | NGrSQAHNlrkaGValS | 1778.99 | 12.01 | 3 | 0 | 62940 | 60035 | 61488 |
| 16 | YGFPSArVNrYwNrHDa | 2109.29 | 9.98 | 2 | 8480 | 60363 | 62472 | 61418 |
| 17 | EGlQSSAYNNYwrklVa | 1999.21 | 8.59 | 1 | 8480 | 60241 | 62155 | 61198 |
| 18 | GlYwSAYNPwrHValaS | 1991.24 | 8.6 | 1 | 13980 | 60848 | 57506 | 59177 |
| 19 | GGrSVSANlQrErkVaG | 1785 | 11.71 | 3 | 0 | 55679 | 58087 | 56883 |
| 20 | kGSNArkNrrDaSGVal | 1800.01 | 11.72 | 4 | 0 | 52284 | 43467 | 47876 |

In certain example embodiments, the AMH receptor binding peptides may be a fragment of any one of the peptides having the sequence set forth as SEQ ID NOS:1-20, the fragment retaining the function of the full-length peptide from which it was derived. For example, as shown in Table 1, amino acids 15, 16, and 17 of SEQ ID NOS: 1-20 have a strong overrepresentation of C-terminal G, S, L, A, V residues across the sequences. It is believed, for example, that such overrepresentation may be due to bias associated with the method for identifying the sequences. Hence, functional fragments of the AMH receptor binding peptides described herein can include, but are not limited to, any of amino acid residues 1-14 of SEQ ID NOS: 1-20, or, in certain example embodiments, peptides having at least 80%, 85%, 90%, 95%, 97%, or 98% sequence identity to amino acids 1-14 of any one of SEQ ID NOS: 1-20. As such, any of the uses, functions, compositions, and methods of the AMH receptor binding peptides described herein can, in certain example embodiments, be achieved via a peptide having 80%, 85%, 90%, 95%, 97%, or 98% sequence identity to amino acids 1-14 of any one of SEQ ID NOS: 1-20. In certain example embodiments, functional fragments include fragments of any one or more peptides having 80%, 85%, 90%, 95%, 97%, or 98% sequence identity to amino acids 1-14 of SEQ ID NOS: 1-20.

In certain example embodiments, the amino acids forming all or a part of the AMH receptor binding peptides described herein may be modifications of naturally occurring amino acids, non-naturally occurring amino acids, post-translationally modified amino acids, enzymatically synthesized amino acids, derivatized amino acids, constructs or structures designed to mimic amino acids, and the like. For example, the amino acids forming the AMH receptor binding peptides can be one or more of the 20 common amino acids found in naturally occurring proteins, or one or more of the modified and unusual amino acids.

In certain example embodiments, each of the amino acids of SEQ ID NOS:1-20 can be L-form amino acids. In certain example embodiments, one or more of the amino acids forming all or a part of the AMH receptor binding peptides described herein can be stereoisomers. That is, any one or more of the amino acids of the AMH receptor binding peptides may be a D- or L-amino acid. As shown in Table 1, for example, certain D-form amino acids are represented by a lower-case letter for the amino acid designation. For example, in SEQ ID NO: 1, the arginine at position 10 can be a D-form amino acid. As such, in certain example embodiments, the AMH receptor binding peptides described herein can have the amino acid sequences shown in SEQ ID NOS: 1-20, such as with the corresponding D-form amino acids as shown in Table 1 (lower case letters). Alternatively, one or more of the amino acids shown in the D-form in Table 1 (lower case letters), for example, can be an L-form amino acid.

Additionally or alternatively, the AMH receptor binding peptides described herein can have other D-form amino acids not shown in Table 1. For example, the AMH receptor binding peptides described herein may include one or more D-form Tryptophan, Leucine, Arginine, Alanine, or other stereoisomers. And in certain example embodiments, the AMH receptor binding peptides do not include any D-form amino acids. That is, the AMH receptor binding peptides can have the same sequence—or share 80%, 85%, 90%, 95%, 97%, or 98% identity—with any one of the sequences set forth as SEQ ID NOS: 1-20 but include only L-form amino acids. Indeed, without being bound by any particular theory or mechanism of action, it is believed that the substitution of one or more L-form amino acids with one or more D-form amino does not affect the function of the AMH receptor binding peptides. Rather, such substitutions are believed to confer higher stability against enzymatic degradation, thus enhancing the durability of the AMH receptor binding peptides as biomaterials.

In certain example embodiments, the AMH receptor binding peptides or functional fragments thereof can also include one or more modified amino acids. The modified amino acid may be a derivatized amino acid or a modified and unusual amino acid. Examples of modified and unusual amino acids include but are not limited to, 2-Aminoadipic acid (Aad), 3-Aminoadipic acid (Baad), β-Amino-propionic acid (Bala, β-alanine), 2-Aminobutyric acid (Abu, piperidinic acid), 4-Aminobutyric acid (4Abu), 6-Aminocaproic acid (Acp), 2-Aminoheptanoic acid (Ahe), 2-Aminoisobutyric acid (Aib), 3-Aminoisobutyric acid (Baib), 2-Aminopimelic acid (Apm), 2,4-Diaminobutyric acid (Dbu), Desmosine (Des), 2,2'-Diaminopimelic acid (Dpm), 2,3-Diaminopropionic acid (Dpr), N-Ethylglycine (EtGly), N-Ethylasparagine (EtAsn), Hydroxylysine (Hyl), allo-Hydroxylysine (Ahyl), 3-Hydroxyproline (3Hyp), 4-Hydroxyproline (4Hyp), Isodesmosine (Ide), allo-Isoleucine (Alle), N-Methylglycine (MeGly, sarcosine), N-Methylisoleucine (MeIle), 6-N-Methyllysine (MeLys), N-Methylvaline (MeVal), Norvaline (Nva), Norleucine (Nle), and Ornithine (Orn). Other examples of modified and unusual amino acids are described generally in Synthetic Peptides: A User's Guide, Second Edition, April 2002, Edited Gregory A. Grant, Oxford University Press; Hruby V J, Al-obeidi F and Kazmierski W: *Biochem J* 268:249-262, 1990; and Toniolo C: *Int J Peptide Protein Res* 35:287-300, 1990; the teachings of all of which are expressly incorporated herein by reference.

In certain example embodiments, the amino acid sequence of the AMH receptor binding peptides is sequential, without any modified and unusual amino acids interrupting the sequence of D- or L-amino acids. In other embodiments, the sequence may include one or more modified and unusual amino acids as noted above. For example, the sequence of the peptides may be interrupted by one or more modified and unusual amino acids. Accordingly, provided are pseudopeptides and peptidomimetics, including structures that have a non-peptidic backbone. In certain example embodiments, the AMH receptor binding peptides include dimers or multimers of peptides that have enhanced affinity for the AMH receptor compared to their monomers.

In certain example embodiments, the AMH receptor binding peptides can be detectably labeled. For example, the AMH receptor binding peptides can be conjugated to an agent used in imaging, research, therapeutics, theranostics, pharmaceuticals, chemotherapy, and radiotherapy. In some embodiments, one or more of the AMH receptor binding peptides are conjugated to or fused with detectable agents, such as a fluorophore, a near-infrared dye, a contrast agent, a nanoparticle, a metal-containing nanoparticle, a metal chelate, an X-ray contrast agent, a PET agent, a metal, a radioisotope, a dye, radionuclide chelator, or another suitable material that can be used in imaging. Examples of a chemiluminescent agent include an enzyme that produces a chemiluminescent signal in the presence of a substrate(s) that produce chemiluminescent energy when reacted with the enzyme. Examples of such an enzyme include horseradish peroxidase (HRP) and alkaline phosphatase (AP). Other examples of a chemiluminescent agent include a non-enzymatic direct chemiluminescent label, such as the Acridinium ester system. Examples of a calorimetric agent include an enzyme such as horseradish peroxidase, alkaline phosphatase, and acetylcholine esterase (AChE). One example of an energy transfer agent is fluorescent lanthanide chelates; fluorescent dyes may be used as fluorescent agents. Representative radioisotopes include 125I, 14C and 3H. In certain example embodiments, the detectable agent linked to one or more of the AMH receptor binding peptides is a fluorescent dye. In some example embodiments, 1, 2, 3, 4, 5, 6, 7, 8, 9, or 10 detectable agents can be linked to one or more of the AMH receptor binding peptides.

As those skilled in the art will appreciate, such detectable agents can produce a detectable signal that is measured using methods known in the art. In certain example embodiments, the measurements can then be used to determine the amount of an analyte in a sample using standard techniques. As such, because of their affinity to the AMH receptor, in certain example embodiments the compositions and methods disclosed herein are useful to measure an amount of Anti-Mullerian Hormone in a sample from a subject. In certain example embodiments, the AMH receptor binding peptides can be used in situ or in vivo to identify the AMH receptor. For example, one or more of the AMH receptor binding peptides describe herein can be detectably labeled. Thereafter, the detectably labeled AMH receptor binding peptides can be used to contact a sample, such as a histology slide or fluid sample. The label can then be detected by conventional means, thereby facilitating identification of the AMH receptor, such as on the slide or in the fluid sample. For example, the location of an AMH receptor in a slide can be identified via the AMH receptor binding peptide binding to the AMH receptor and the detection of a label that is attached to the AMH receptor binding peptide.

In certain example embodiments, the AMH receptor binding peptides described herein can be synthetically produced using known techniques for peptide synthesis. For example, AMH receptor binding peptides can be synthesized by chemical synthesis using solid phase peptide synthesis. These methods employ either solid or solution phase synthesis methods (see for example, J. M. Stewart, and J. D. Young, Solid Phase Peptide Synthesis, 2nd Ed., Pierce Chemical Co., Rockford Ill. (1984) and G. Barany and R. B. Merrifield, The Peptides: Analysis Synthesis, Biology editors E. Gross and J. Meienhofer Vol. 2 Academic Press, New York, 1980, pp. 3-254 for solid phase synthesis techniques; and M Bodansky, Principles of Peptide Synthesis, Springer-Verlag, Berlin 1984, and E. Gross and J. Meienhofer, Eds., The Peptides: Analysis, Synthesis, Biology, suprs, Vol 1, for classical solution synthesis.

In certain example embodiments, AMH receptor binding peptides described herein can be prepared by standard chemical or biological means of peptide synthesis. Biological methods include, without limitation, expression of a nucleic acid encoding a peptide in a host cell or in an in vitro translation system. Hence, in certain example embodiments, also provided are isolated nucleic acid molecules encoding each of the AMH receptor binding peptides described herein or function fragments thereof. For example, the nucleic acid molecules include a nucleic acid sequence encoding an amino acid sequence at least 75%, 80%, 85%, 90%, 95% identical to the amino acids set forth as any one of SEQ ID NOS: 1-20, such as at least 95%, at least 96%, at least 97%, at least 98%, at least 99%, or 100% identical to the amino acids set forth as any one of SEQ ID NOS: 1-20. In the context of the compositions and methods described herein, a nucleic acid sequence that encodes at least one AMH receptor binding peptides or functions fragment as described herein can be incorporated into a vector capable of expression in a host cell (for example an adenoviral vector), using established molecular biology procedures. Such methods are known in the art, for example, and can be used to express one or more the AMH receptor binding peptides or functional fragments thereof as described herein.

The isolated nucleic acid may include any type of nucleic acid, including, but not limited to DNA and RNA. For example, in one embodiment, the composition includes an isolated DNA molecule, including for example, an isolated cDNA molecule, encoding a peptide of the invention, or functional fragment thereof. In one embodiment, the composition includes an isolated RNA molecule encoding a peptide of the invention, or a functional fragment thereof. The isolated nucleic acids may be synthesized using any method known in the art.

In certain example embodiments, the nucleic acid molecules can be modified to improve stability in serum or in growth medium for cell cultures. Modifications of the nucleic acid of the invention may be present at one or more of, a phosphate group, a sugar group, backbone, N-terminus, C-terminus, or nucleobase. Modifications can be added to enhance stability, functionality, and/or specificity and to minimize immunostimulatory properties of the nucleic acid molecule of the invention. For example, in order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect function of the molecule.

In certain example embodiments, the nucleic acid molecule may contain at least one modified nucleotide analogue. For example, the ends may be stabilized by incorporating modified nucleotide analogues. Non-limiting examples of nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In preferred backbone-modified ribonucleotides the phosphoester group connecting to adjacent ribonucleotides is replaced by a modified group, e.g., of phosphothioate group. In preferred sugar-modified ribonucleotides, the 2' OH-group is replaced by a group selected from H, OR, R, halo, SH, SR, NH2, NHR, NR2 or ON, wherein R is C1-C6 alkyl, alkenyl or alkynyl and halo is F, Cl, Br or I.

In certain example embodiments, provided are vectors in which the isolated nucleic acids described herein can be inserted. The art is replete with suitable vectors that are useful in the present invention. For example, the expression of natural or synthetic nucleic acids encoding a peptide is typically achieved by operably linking a nucleic acid encoding the peptide or portions thereof to a promoter and incorporating the construct into an expression vector. The vectors to be used are suitable for replication and, optionally, integration in eukaryotic cells. Typical vectors contain transcription and translation terminators, initiation sequences, and promoters useful for regulation of the expression of the desired nucleic acid sequence.

Compositions & Formulations

In certain example embodiments, provided is a pharmaceutical composition or formulation including one or more of the AMH receptor binding peptides or functional fragments thereof described herein. Such a pharmaceutical composition can be a combination of any peptide described herein with other chemical components, such as carriers, stabilizers, diluents, dispersing agents, suspending agents, thickening agents, antioxidants, solubilizers, buffers, osmolytes, salts, surfactants, amino acids, encapsulating agents, bulking agents, cryoprotectants, and/or excipients. The pharmaceutical composition facilitates administration of a peptide described herein to an organism, such as a subject.

As those skilled in the art will appreciate, pharmaceutical compositions including one or more of the AMH receptor binding peptides or fragments thereof can be administered in therapeutically-effective amounts as pharmaceutical agents or compositions by various forms and routes including, for example, intravenous, subcutaneous, intramuscular, rectal, aerosol, parenteral, ophthalmic, pulmonary, transdermal, vaginal, optic, nasal, oral, sublingual, inhalation, dermal, intrathecal, intranasal, and topical administration. A pharmaceutical composition can be administered in a local or systemic manner, for example, via injection of the peptide described herein directly into an organ, optionally in a depot.

Parenteral injections can be formulated for bolus injection or continuous infusion. The pharmaceutical compositions can be in a form suitable for parenteral injection as a sterile suspension, solution or emulsion in oily or aqueous vehicles, and can contain formulatory agents such as suspending, stabilizing and/or dispersing agents. Pharmaceutical formulations for parenteral administration include aqueous solutions of a peptide described herein in water-soluble form. Suspensions of peptides described herein can be prepared as oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. The suspension can also contain suitable stabilizers or agents which increase the solubility and/or reduce the aggregation of such peptides described herein to allow for the preparation of highly concentrated solutions. Alternatively, the peptides described herein can be lyophilized or in powder form for re-constitution with a suitable vehicle, e.g., sterile pyrogen-free water, before use. In some embodiments, a purified peptide is administered intravenously.

In certain example embodiments, one or more of the AMH receptor binding peptides or functional fragments thereof described herein can be applied directly to an organ, or an organ tissue or cells, such as cancer cells, during a surgical procedure. Additionally or alternatively, one or more of the AMH receptor binding peptides described herein can be administered topically and can be formulated into a variety of topically administrable compositions, such as solutions, suspensions, lotions, gels, pastes, medicated sticks, balms, creams, and ointments. Such pharmaceutical compositions can contain solubilizers, stabilizers, tonicity enhancing agents, buffers and preservatives.

Pharmaceutical compositions can be formulated using one or more pharmaceutically-acceptable carriers including excipients and auxiliaries, which facilitate processing of the active compounds into preparations that can be used pharmaceutically. Formulation can be modified depending upon the route of administration chosen. For example, the pharmaceutical compositions including a peptide described herein can be manufactured by synthesizing the peptide and then lyophilizing the peptide and/or mixing, dissolving, granulating, levigating, emulsifying, encapsulating the peptide. In certain example embodiments, the pharmaceutical compositions can include at least one pharmaceutically acceptable carrier, diluent, or excipient and compounds described herein as free-base or pharmaceutically-acceptable salt form.

Methods for the preparation of the compositions described herein can include formulating one or more of the AMH receptor binding peptide described herein with one or more inert, pharmaceutically-acceptable excipients or carriers to form a solid, semi-solid, or liquid composition. Solid compositions include, for example, powders, tablets, dispersible granules, capsules, cachets, and suppositories. These compositions can also contain minor amounts of nontoxic, auxiliary substances, such as wetting or emulsifying agents, pH buffering agents, and other pharmaceutically acceptable additives. Non-limiting examples of pharmaceutically-acceptable excipients can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), each of which is incorporated by reference in its entirety.

In certain example embodiments, provided is a kit, the kit including one or more of the AMH receptor binding peptides or functional fragments thereof. For example, the kit can include a pharmaceutical composition or formulation, the pharmaceutical composition or formulation including the one or more of the AMH receptor binding peptides or functional fragments thereof as described herein. The kit can also include, for example, packaging and optionally instructions for administration of the one or more AMH receptor binding peptides or functional fragments thereof (or composition or formulation thereof) to a subject. In certain example embodiments, the kit may be organized to indicate a single formulation or combination of formulations to be taken at each desired treatment regimen as specified in written instructions encompassed in the kit.

Methods of Use and Treatment

As those skilled in the art will appreciate and as described herein, AMH acts as an inhibitory hormone in all its currently known functions. For example, recombinant AMH regulates ovarian cortex function through modulation of hormone receptors other than the AMH receptor [9]. AMH also regulates the ovarian cortex's sternness potential in fresh and vitrified/thawed ovarian cortex [9]. In certain example embodiments, as peptides that can mimic the function and effects of AMH, it is believed that administration of one or more of the AMH receptor binding peptides described herein can modulate these and other physiological functions that are otherwise mediated by AMH. In certain example embodiments, one or more of the AMH receptor binding peptides may bind to the AMH receptor but not activate the receptor, thereby functioning as an AMH receptor antagonist. In certain example embodiments, the action of the AMH receptor binding peptide or functional fragment thereof may be tissue or cell specific. Hence, the AMH receptor binding peptides described herein or functional fragments thereof, whether an AMH receptor agonist or antagonist, can be used to modulate physiological and pathophysiological conditions in a subject that are otherwise regulated or affected by AMH.

Accordingly, in certain example embodiments provided herein are methods for modifying the activity of the AMH receptor, the method including administering one or more of the AMH receptor binding peptides described herein or a functional fragment thereof. Also provided herein are methods of treating one or more disease states or conditions, and/or treating and/or modifying one or more physiological states, related to activation or regulation of the AMH receptor pathway. Examples of such methods of treatment and use include modification of fertility in females, treatment of precocious puberty in females, delay of natural menopause, preservation of ovarian follicular reserve, use in contraception, use in fertility preservation after ovarian cortex transplant, treatment of endometriosis, use in male fertility preservation, use in the treatment of cancer treatment and/or prevention, and/or treatment of polycystic ovary syndrome (PCOS). For example, provided are methods seek to reduce or inhibit recruitment of primordial follicles into the pool of growing follicles, such as to obtain contraception and/or prolong the duration of fertility and/or postpone the menopause. Indeed, as those skilled in the art will appreciate based on this disclosure, the AMH receptor binding peptides or functional fragments thereof described herein can be used for any purpose for which physiological modification of the AMH receptor activity is desired or needed.

In certain example embodiments, provided are methods and compositions for treating a female subject to modify her fertility, the method including administering to the female subject one or more of the AMH receptor binding peptides described herein or functional fragments thereof in an amount effective to modify fertility. In certain example embodiments, administration of the one or more of the AMH receptor binding peptides described herein inhibit recruitment of primordial follicles into the pool of growing follicles. In certain example embodiments, such as when the one or more of the AMH receptor binding peptides described herein functions as an antagonist, can be used to promote recruitment of primordial follicles into the pool of growing follicles, for example to treat ovarian failure.

In certain example embodiments, provided is a method of inhibiting follicle activation in subject undergoing ovary transplantation, the method including administering to a subject a therapeutically effective amount of a pharmaceutical composition including one or more of the AMH receptor binding peptides described herein. In certain example embodiments, administration of the one or more of the AMH receptor binding peptides described herein obtain contraception and/or prolong the duration of fertility and/or postpone the menopause. In certain example embodiments, a different contraceptive is co-administered.

In certain example embodiments, provided are methods and compositions for modulating folliculogenesis, such as modulating that the expression of or activity of endogenous AMH. That is, in certain example embodiments, one or more of the AMH receptor binding peptides described herein or functional fragments thereof can be administered to a subject to a subject to modulate the activity and/or expression of AMH in the subject, thereby modulating folliculogenesis in the subject. Without wishing to be bound by any particular theory, it is believed that the administration of the one or more of the AMH receptor binding peptides described herein or functional fragments thereof mimics the effects of AMH, thereby modulating folliculogenesis.

In certain example embodiments, provided are methods and compositions for modulating the function of granulosa cells in the subject. For example, one or more of the AMH receptor binding peptides described herein or functional fragments thereof can be administered to a subject to a subject to modulate the activity and function of the granulosa cells, such as by modulating the expression of AMH, Inhibin A/B, the AMH receptor, and/or the FSH receptor in the subject. In certain example embodiments, the administration of the one or more of the AMH receptor binding peptides described herein or functional fragments thereof can reduce the expression of AMH, Inhibin A/B, the AMH receptor, and/or the FSH receptor in the subject. In certain example embodiments, the administration of the one or more of the AMH receptor binding peptides described herein or functional fragments thereof can affect other markers of granulosa cell function.

In certain example embodiments, provided are methods and compositions of treating a subject having impaired fertility or at risk for impaired fertility. The method includes, for example, administering to the subject an effective amount of a composition as described herein which can function as an AMH-replacement therapy. For example, in certain embodiments the method includes administering one or more of the AMH receptor binding peptides or functional fragments thereof to the subject. In certain example embodiments, provided is a treatment of a subject with diminished ovarian reserve (DOR) or premature ovarian aging, which is characterized by reduced number of follicles available for maturation and ovulation. Certain subjects with diminished ovarian reserve have a decreased level of AMH, which results in unchecked initiation of primordial follicle growth thereby resulting in a rapid depletion of follicles. Treatment of a subject with a diminished ovarian reserve or at risk for a diminished ovarian reserve with one or more of the AMH receptor binding peptides or functional fragments thereof can, for example, slow the development of follicles.

In certain example embodiments, the methods of treatment or use described herein include administering a therapeutically effective amount of one or more of the AMH receptor binding peptides or functional fragments thereof. For example, a pharmaceutical composition including one or more of the AMH receptor binding peptides described herein can be administered to a subject suffering from one or more physiological or pathophysiological conditions described herein. And as those skilled in the art will appreciate based on this disclosure, a therapeutically effective amount can vary widely depending on the severity of the condition, the age and relative health of the subject, the potency of the compounds used, and other factors.

In certain example embodiments, the therapeutically effective amount of the pharmaceutical composition is determined based on the intended goal, for example, such as an amount sufficient to delay menopause, prevent precocious puberty, provide contraception, treat endometriosis, and/or to inhibit tumor or cancer cell growth. As such, the appropriate dose will vary depending on the characteristics of the subject, for example, whether the subject is a human or non-human, the age, weight, and other health considerations pertaining to the condition or status of the subject, the mode, route of administration, and number of doses, and whether the pharmaceutical composition includes nucleic acids or viruses. In certain example embodiments, a unit dosage can be about 0.1 to about 10 mg per subject per day. Dosages from about 0.1 up to about 100 mg per subject per day may be used, particularly if the agent is administered to a secluded site and not into the circulatory or lymph system, such as into a body cavity, or into a lumen of an organ. In certain example embodiments, one or more of the AMH receptor binding peptides described herein can be administered via a controlled release, such as in a controlled release formulation.

In certain example embodiments, one or more of the AMH receptor binding peptides described herein or functional fragments thereof can be administered to the subject at a dose of about 10 ng/day to about 100,000 ng/day. In certain example embodiments, the AMH receptor binding peptides described herein or functional fragments thereof can be administered to the subject at a dose of about 50 ng/day to about 50,000 ng/day. In certain example embodiments, the AMH receptor binding peptides described herein or functional fragments thereof can be administered to the subject at a dose of about 100 ng/day to about 50,000 ng/day. In certain example embodiments, the AMH receptor binding peptides described herein or functional fragments thereof is administered to the subject at a dose of about 10,000 ng/day to about 40,000 ng/day. In certain example embodiments, the AMH receptor binding peptides described herein or functional fragments thereof can be administered to the subject at a dose of about 5,000 ng/day, 10,000 ng/day, 15,000 ng/day, 20,000 ng/day, about 25,000 ng/day, about 30,000 ng/day, about 35,000 ng/day, about 40,000 ng/day, about 45,000 ng/day, or 50,000 ng/day.

In certain example embodiments, one or more of the AMH receptor binding peptides described herein or functional fragments thereof can be administered to the subject for about 1 day to about 350 days. In certain example embodiments, one or more of the AMH receptor binding peptides described herein or functional fragments thereof can be administered to the subject for about 10 days to about 180 days. In certain example embodiments, one or more of the AMH receptor binding peptides described herein or functional fragments thereof can be administered to the subject for about 30 days to about 90 days. In certain example embodiments, one or more of the AMH receptor binding peptides described herein or functional fragments thereof can be administered to the subject for about 30 days, about 40 days, about 50 days, about 60 days, about 70 days, about 90 days. In certain example embodiments, the one or more of the AMH receptor binding peptides described herein or functional fragments thereof can be administered to the subject indefinitely or for several years.

In certain example embodiments, single or multiple administrations of the compositions are administered depending on the dosage and frequency as required and tolerated by the subject. In one embodiment, for example, the dosage is administered once as a bolus, but in another embodiment can be applied periodically until a therapeutic result is achieved. Generally, the dose is sufficient to treat or ameliorate symptoms or signs of disease without producing unacceptable toxicity to the subject. Systemic or local administration can be also utilized.

In certain examples, a subject may be treated as described herein via the administration of an initial dose of one or more of the AMH receptor binding peptides, and thereafter placed on a maintenance dose. The maintenance dose, for example, can be more or less than the initial dose. In certain example embodiments, an optimal dose to be given and an optimal dosage regimen can be easily determined by persons skilled in the art. Doses and dosage regimen may be varied according to various parameters, such as the effect sought and the age, weight and condition of the subject to be treated. In certain example embodiments, the AMH receptor binding peptides or functional fragments thereof described herein can be administered to healthy subjects of various ages, during time periods ranging from days to years.

In certain example embodiments, a subject may be treated via the administration of an initial dose of one or more of the AMH receptor binding peptides described herein, and then one or more markers of AMH activity can be measured to determine the subject's response. Based on the subject's response, for example, a maintenance dose can thereafter be determined and administered to the subject and such a way to maintain the level of one or more response markers. Such markers can additionally or alternatively be assessed, for example, while the subject is on a maintenance dose or after the subject completes a treatment regimen. Additionally or alternatively, a subject's response may be determined qualitatively, such as by the fact that the subject does not get pregnant or that symptoms related to menopause are deuced following the administration of the one or more AMH receptor binding peptides as described herein.

In certain example embodiments, administration of one or more of the AMH receptor binding peptides described herein can modify or otherwise affect one or more markers associated with the AMH-receptor pathway. For example, in certain example embodiments administration of one or more of the AMH receptor binding peptides or functional fragments thereof may reduce or otherwise modify the levels of Inhibin A or B, such as the expression of Inhibin A or B and/or the serum levels of Inhibin A or B. For example, administration of one or more of the AMH receptor binding peptides described herein may reduce serum levels of Inhibin A or B in a subject by about 10%, 15%, 20%, 25%, 30%, 35%, 40%, 45%, 50%, 55%, 60%, 65%, 70%, 75%, or 80% or more as compared to baseline levels of Inhibin levels in the subject.

Additionally or alternatively, administration of one or more of the AMH receptor binding peptides or functional fragments thereof may reduce the expression of the AMH-R2 or FSH receptors. Additionally or alternatively, in certain example embodiments administration of one or more of the AMH receptor binding peptides or functional fragments thereof may reduce markers of cellular proliferation (e.g., Ki67) or apoptosis (e.g., caspase3). In certain example embodiments, administration of one or more of the AMH receptor binding peptides described herein to a subject can modify or otherwise affect the level of estradiol in the subject. For example, with the administration of one or more of the AMH receptor binding peptides, serum estradiol levels may decrease, such as by 10%, 15%, 20%, 25%, 30%, 35%, 40%, 45%, 50%, 55%, 60%, 65%, 70%, 75%, or 80%. Additionally or alliteratively, administration of one or more of the AMH receptor binding peptides describe herein may reduce endogenous AMH levels, such as by 10%, 15%, 20%, 25%, 30%, 35%, 40%, 45%, 50%, 55%, 60%, 65%, 70%, 75%, or 80%.

In certain example embodiments, the activity and/or function of the AMH receptor binding peptides described herein or functional fragment thereof can be readily determined by one or more methods known in the art. For example, one or more known methods can be used to assess the agonistic or antagonistic effect of one or more of the AMH receptor binding peptides described herein or functional fragment thereof. Such methods include, for example, culture of urogenital ducts isolated from embryos or fetuses from pregnant wild type and AMH knockout strains. These ducts can be incubated with various AMH preparations and the regression of the Müllerian ducts can be assessed (MacLaughlin et al. 1992, Endocrinology 131: 291-296). Additionally or alternatively, activity and/or function can be determined via incubation of HEK293 cells stably transfected with cDNAs encoding AMH type II receptor cDNA, AMH type I receptor (Alk2), a reporter construct containing the aromatase promoter linked to luciferase cDNA, FSH receptor cDNA (all cDNAs can be taken from different species, including rodents and human). The inhibitory effect of AMH on the FSH-induced aromatase-luciferase response is the parameter to be determined in this system (our observations). This system can be used to test the various AMH preparations.

Treatment of Precocious Puberty in Females

As those skilled in the art will appreciate, hyperproduction of follicle-stimulating hormone (FSH) from the pituitary gland, neoplasia, or parenteral, stimulates granulosa cells to initiate their follicular development during childhood, thus increasing production of estrogen, thereby resulting in precocious puberty. FSH, however, can act only on granulosa cells from follicles that have already initiated their development from primordial follicles (such as, in sequence, primary, secondary, and tertiary follicles). Since AMH's functions include inhibiting this first developmental step from primordial to primary follicles as well as inhibiting further size increase of tertiary follicles, the increased FSH would not have suitable follicles to stimulate, thereby ultimately decreasing the amount of estrogen production.

Accordingly, in certain example embodiments provided herein is a method of treating precocious puberty in a subject, the method including the administration of one or more of the AMH receptor binding peptides described herein to the subject. That is, one or more of the AMH receptor binding peptides described herein or functional fragments thereof can be used to treat precocious puberty, including, for example, central precocious puberty, precocious puberty from McCune Albright syndrome, or precocious puberty arising from intracranial masses.

Without being bound by any particular theory, it is believed that one or more of the AMH receptor binding peptides described herein can be used inhibit of the developmental step from primordial to primary follicles, thereby reducing the effects of FSH and hence inhibiting the production of excess estrogen. As such, in certain example embodiments provided are methods for treating precocious puberty in a female subject, the methods including administering one or more of the AMH receptor binding peptides described herein to a subject suffering from (or suspected to be suffering from) precocious puberty, thereby reducing the amount of excess estrogen in the subject and hence treating the precocious puberty in the subject. In such example embodiments, the one or more AMH receptor binding peptides can be an AMH receptor agonist, such as an AMHR2 agonist, thereby mimicking the effect of AMH binding to the AMH receptor in the subject. By mimicking the effects of AMH, the one or more AMH receptor binding peptides inhibit of the developmental step from primordial to primary follicles in the subject, thereby reducing the effects of FSH and hence inhibiting the production of excess estrogen in the subject.

In certain example embodiments, to treat precocious puberty in females, the method includes identifying a female subject suffering from precocious puberty and administering to the subject an effective amount of the AMH receptor binding peptides identified in Table 1 or functional fragments thereof. Thereafter, the subject can be monitored, for example, to determine any improvement in precocious puberty symptoms, such as a reduction in one or more specific symptoms associated with the precocious puberty. For example, administration of one or more AMH receptor binding peptides described herein may reduce symptoms such as early breast development, early development of pubic or underarm hair, rapid height growth, excessive and early acne, body order, vaginal discharge or bleeding, or other signs and symptoms of precocious puberty in females.

In certain example embodiments, the AMH receptor binding peptides described herein can be co-administered with other drugs or compositions known to treat precocious puberty, such as gonadotropin-releasing hormone (GnRH) analog therapies. Such therapies typically include injections of a medication, such as histrelin (Vantas™ and Supprelin LA™), leuprolide acetate (Lupron Depot™), or triptorelin (Trelstar™, Triptodur Kit™), Goserelin (Zoladex™), which can delay further development. Hence, in certain example embodiments, treating preconscious puberty in the female includes the administration of one or more AMH receptor binding peptides described herein alone, or in addition to, the administration of an GnRH agonist.

Delay of Menopause

Menopause is a major milestone in the ageing process in women. Yet unfortunately, the cessation of ovarian function and the almost complete absence of female sex steroid hormone production by the ovaries in postmenopausal life contributes to increased manifestation of osteoporosis, cardiovascular disease, and Alzheimer's disease. Menopause ensues when all follicles in the ovaries are depleted. That is, menopause is caused by the exhaustion of the pools of ovarian follicles. The process of depletion is mediated by apoptosis (i.e., spontaneous cell death) and coexists with the cyclic follicular development of primary, secondary, and tertiary follicles. Primordial follicles, instead, do not undergo apoptosis and constitute the so-called ovarian reserve. It is calculated that, during a woman's reproductive life, per each ovulated follicle (i.e., per each menstrual cycle) another 1,000 follicles undergo apoptosis until menopause at age 51. Apoptosis involves more follicles as age progresses because of the progressive decrease of AMH (hence more primordial follicles will initiate development to primary follicles).

In certain example embodiments, provided is a method of delaying menopause in a female subject, including reducing or ameliorating the symptoms associated with menopause, the method including the administration of one or more of the AMH receptor binding peptides described herein to the subject. That is, one or more of the AMH receptor binding peptides described herein can be used to delay menopause, thereby also treating the numerous adverse physiological events and conditions associated with menopause, such as osteoporosis, cardiovascular disease, and Alzheimer's disease.

Without wishing to be bound by any particular theory or mechanism of action, it is believed that, like native AMH, administration of one or more of the AMH receptor binding peptides described herein—such as one or more of the AMH receptor binding peptides that act as AMH receptor agonists or fragments thereof—to a female subject can inhibit the first step in follicular development from primordial to primary follicles. Hence, it is believed that the administration of one or more of the AMH receptor binding peptides described herein to the female subject can preserve the ovarian reserve for as long as they are administered to the female subject. For example, if the one or more AMH receptor binding peptides described herein are administered for about 5 years, the onset of menopause can be delated for about 5 years. If the one or more AMH receptor binding peptides described herein are administered for about 10 years, the onset of menopause can be delayed for about 10 years.

As such, the delay of menopause can correlate to the length of time of the one or more AMH receptor binding peptides described herein are administered to the female subject. In certain example embodiments, the one or more AMH receptor binding peptides or functional fragments thereof described herein are administered for 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more years, thereby delaying menopause for a corresponding number of years and/or preventing menopause from every developing. In certain example embodiments, to delay menopause one or more the AMH receptor binding peptides described herein can be administered 1, 2, 3, or 4 more years post-menarche, after the female completes her sexual development, and thereafter for as long menopause is sought to be delayed.

In certain example embodiments, one or more of the AMH receptor binding peptides or functional fragments thereof described herein can be co-administered with an estrogen and/or progesterone hormone when delaying menopause. Such hormone co-administration, for example, can provide estrogen/progesterone replacement during the AMH receptor binding peptide administration period. It is believed, for example, that such co-administration is beneficial, for example, because the AMH receptor binding peptide alone can arrest ovarian function, hence producing a hypo-estrogenic and a-progestinic environment (fatty cells produce small amounts of estrogen but no progesterone), thus causing problems such as bone loss and uterine hypoplasia. Co-administration of the AMH receptor binding peptides described herein along with estrogen/progesterone replacement, contained in commercially available combination birth-control pills (e.g., Lo-Estrin®, Kelnor®, or Yasmin®), would prevent such problems. In specific cases where also a hypo-androgenic state manifests with loss of libido, for example, co-administration of androgenic compounds, such as commercially available DHEA (de-hydro-epiandrosterone), or testosterone, would be beneficial.

As those skilled in the art will appreciate, delaying menopause via AMH receptor binding peptide administration as described herein can also delay or lesson the direct symptoms of menopause, such as irregular periods, vaginal dryness, hot flashes, chills, night sweats, sleep problems, mood changes, weight gain and slowed metabolism, thinning hair and dry skin, and loss of breast fullness. Further, use of one or more of the AMH receptor binding peptide described herein to delay menopause to age about age 55-65, for example, could prevent multiple post-menopausal health problems, including osteoporosis, heart disease, breast cancer, endometrial cancer, ovarian cancer, memory loss, dementia.

Preservation of Ovarian Follicular Reserve

Female infertility has many causes, including tubal disease, anovulation, decreased endometrial receptivity, and decreased ovarian reserve. The latter is due to premature depletion of ovarian follicles, which causes fewer follicles to be susceptible for natural, or iatrogenic, maturation. The causes for this phenomenon are multiple and include, for example, aging after 35 years, autoimmune conditions, Fragile X pre-mutation, endometriosis, pelvic inflammation from different sources. Destruction of ovarian follicle reserve is also a significant side effect of various acute insults, such chemotherapy. Indeed, the impact of chemotherapy on fertility is directly dependent on the survival or loss of the dormant oocytes in the primordial follicles that include the ovarian follicle reserve. In the short term, chemotherapy includes temporary amenorrhea, while in the long-term chemotherapy damages the primordial follicle pool. This damage can cause total loss of the primordial follicle pool resulting in sterilization, but more often the loss is partial resulting in a reduced primordial follicle pool.

Accordingly, in certain example embodiments provided is a method of preserving the ovarian follicle pool in a subject, the method including the administration of one or more of the AMH receptor binding peptides described herein to the subject. That is, provided is a method in which one or more of the AMH receptor binding peptides described herein can be used to preserve ovarian follicular reserve for as many years (thus preventing infertility, especially the one from decreased ovarian reserve). This includes, for example, preservation of the ovarian follicle pool from acute insults, such as those chemotherapy.

Without being bound by any particular theory or mechanism of action, it is believed that—by mimicking the effects of AMH—one or more of the AMH receptor binding peptides described herein can inhibit the first step in follicular development from primordial to primary follicles, hence preserving the ovarian reserve for as long as the AMH receptor binding peptides are administered to a female subject. For example, administration of one or more of the AMH receptor binding peptides described herein as soon as a diagnosis of decreased ovarian reserve is established can arrest ovarian follicle apoptosis until the female is ready to attempt conception with, or without, fertility treatments. As such, in certain example embodiments, administration of one or more of the AMH receptor binding peptides described herein can be used to preserve ovarian reserve for several years, such as 1, 2, 3, 4, 5, 6, 7, 8, 9, 10, 11, 12, 13, 14, 15, 16, 17, 18, 19, 20, 21, 22, 23, 24, or 25 years.

In certain example embodiments, the methods of preserving the ovarian follicle reserve described herein can be used for any female subject who has, or is likely to experience, factors which predispose the female to premature ovarian aging, including iatrogenic factors such as, ovarian surgery, chemotherapy, radiation therapy, bone marrow transplantation, anti-viral therapies and other medical risk factors. In certain example embodiments, the subject can be undergoing chemotherapy, chemo-radiotherapy, radiotherapy or other cancer treatment. By preventing primordial follicles from being recruited, the risk of the primordial follicles being affected by chemotherapy drugs is reduced. Cytotoxic drugs, particularly chemotherapy which damage dividing cells can often be very toxic to growing follicles. The loss of growing follicles causes a deregulation of the negative feedback (i.e., temporarily lowers AMH levels), which leads to an over-recruitment of primordial follicles. Those follicles then also get damaged by the chemotherapeutic agents and the repeated chemotherapy cycle procedures until the ovary is depleted of all primordial follicles. Because women are born with a set number of primordial follicles, premature ovarian failure due to chemotherapy or another condition is irreversible. Thus, the use of the AMH receptor binding peptides described herein or functional fragments thereof includes their administration to cancer patients during or after chemotherapeutic treatment to prevent deregulation and/or to re-establish the negative feedback provided by AMH.

In certain example embodiments, AMH receptor binding peptides described herein or functional fragments thereof can be used to treat a female subject that is pre-disposed to premature ovarian aging (POA). In certain example embodiments, the AMH receptor binding peptides described herein or functional fragments thereof can be used to treat a female subject who has, or is likely to have endometriosis, polycistric ovarian syndrome (PCOS), FMR1 mutations (e.g., measuring CGG repeats in FMR1 gene as disclosed in U.S. Pat. App. 20110020795 and 20140206756, each of which are incorporated herein in their entirety by reference), subjects with less than 26 GCC FMR1 repeats (het-norm/low-sub genome or hom/low/low-sub genome), BRAC1 mutations, turner syndrome, autoimmunity, thyroid autoimmunity (e.g., hyperthyroidism or hypothyroidism), adrenal autoimmunity, any other autoimmunity, autoimmunity polyglandular syndromes, family history of autoimmune disease (e.g., one 1st degree or two 2nd decree relatives), history of repeated pregnancy loss or history of early maternal/sibling menopause.

In certain example embodiments, co-administration of estrogen and/or progesterone hormones, such as an estrogen-containing contraceptive, can be used along with administration of one or more of the AMH receptor binding peptides to preserve ovarian reserve. As described herein, co-administration of estrogen and/or progesterone provide estrogen and/or progesterone replacement during the AMH receptor binding peptide administration period. Such co-administration can be beneficial, for example, because the AMH receptor binding peptide alone can arrest ovarian function, hence producing a hypo-estrogenic and a-progestinic environment (fatty cells produce small amounts of estrogen but no progesterone), thus causing problems such as bone loss and uterine hypoplasia. Co-administration of the AMH receptor binding peptides described herein along with estrogen/progesterone replacement, contained in commercially available combination birth-control pills (e.g., Lo-Estrin®, Kelnor®, or Yasmin®), would prevent such problems.

Contraception

In certain example embodiments, provided is a method of contraception in a female subject, the method including the administration of one or more of the AMH receptor binding peptides described herein to the subject. That is, similar to delaying menopause as describe herein, for example, administration of one or more of the AMH receptor binding peptides—after a female subject completes her sexual development—can inhibit follicular development and hence ovulation, thus interrupting the estrous cycle and providing highly effective contraception.

In certain example embodiments, administration of one or more AMH receptor binding peptides for 10 years, or more, would prevent unwanted pregnancies and delay menopause for the same amount of time. As such, administration of one or more of the AMH receptor binding peptides described herein could be used as an effective contraception for 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more years. This approach to contraception would decrease the number of unwanted pregnancies and abortions. Indeed, use of the AMH receptor binding peptides described herein is advantageous in that, in addition to providing contraception, contraception based on exogenous AMH agonists will be associated with conservation of the pool of primordial follicles as described herein. Conservation of this pool is essential to obtain optimal conditions for a prolonged period of fertility following the end of the contraceptive period.

In certain example embodiments, one or more of the AMH receptor binding peptides or functional fragments thereof described herein can be co-administered with an estrogen and/or progesterone hormone when delaying menopause. Such hormone co-administration, for example, can provide estrogen/progesterone replacement during the AMH receptor binding peptide administration period. It is believed, for example, that such co-administration is beneficial, for example, because the AMH receptor binding peptide alone can arrest ovarian function, hence producing a hypo-estrogenic and a-progestinic environment (fatty cells produce small amounts of estrogen but no progesterone), thus causing problems such as bone loss and uterine hypoplasia. Co-administration of the AMH receptor binding peptides described herein along with estrogen/progesterone replacement, contained in commercially available combination birth-control pills (e.g., Lo-Estrin™, Kelnor™ or Yasmin™), would prevent such problems. In specific cases where also a hypo-androgenic state manifests with loss of libido, for example, co-administration of androgenic compounds, such as commercially available DHEA (de-hydroepiandrosterone), or testosterone, would be beneficial.

Fertility Preservation after Ovarian Cortex Transplant

As those skilled in the art will appreciate, gonadotoxic chemotherapy or radiation for malignant disease can result in altered ovarian function, which can affect both hormonal production and reproductive potential in females. The most severe consequences are premature ovarian insufficient and infertility, which greatly impact quality of life. Restoration of ovarian function, including fertility and endocrine function, would substantially improve the quality of life for women of reproductive age after they have survived cancer and its treatment.

Ovarian freezing and transplantation have garnered increasing interest as a potential way of preserving fertility in cancer patients. Transplantation of frozen-thawed or fresh ovarian tissue or whole ovary is a delicate procedure aimed to restore fertility to patients who have lost ovarian follicle reserve or have poor quality follicles by delivering a stock of resting non growing follicles that can serve in the future to restore and maintain follicular activity and ovulations that may enable future reproduction. A high portion of follicles delivered back to the body by transplantation, however, disappear rapidly due to premature follicle activation. Tissue transplantation of the ovarian cortex, i.e., the outer portion of the ovary where ovarian follicles are located, has also been performed to treat infertility. With ovarian cortex transplant, it has been shown that administration of recombinant AMH in the peri-transplant period after ovarian cortex transplantation decreased apoptosis and cellular activation and regulated stem cell markers tissue expression [9]. Recombinant AMH also effectively preserved the transplanted ovarian cortex tissue for as long as it was administered. However, it did not protect from the initial, non-hormonal dependent, follicular depletion [9].

Accordingly, in certain example embodiments provided is a method of fertility preservation after ovarian cortex transplant in a female subject, the method including the administration of one or more of the AMH receptor binding peptides described herein to the subject. That is, administration of one or more of the AMH receptor binding peptides described herein or functional fragments thereof to a subject can be used to preserve fertility after ovarian cortex transplant. In certain example embodiments, one or more of the e AMH receptor binding peptides or functional fragments thereof described herein can increase graft survival, enable future pregnancy, and prolong hormone secretion. In certain example embodiments, graft survival could be increased by months to years, depending on the size of the grafted fragment or fragments. For example graft survival could be increased by 1, 2, 3, 4, 5, 6, 7, 8, 9, 10, 11 or twelve months, or 2, 3, 5, 10, 15, 20, 25, 30, 35, or 40 years. Thus, in certain example embodiments, the AMH receptor binding peptides or functional fragments described herein are directed to subjects undergoing ovarian tissue transplantation or whole ovary transplantation.

Without being bound by any theory or mechanism of action, it is believed that the process of transplantation is linked to tissue damage such as ischemia, oxidative stress, and fibrosis, all of which have been proposed to induce the follicle activation and loss observed post-transplantation. Accordingly, increasing follicle activation ultimately reduces the reserve of primordial follicles and thereby reduces the lifespan of the transplanted ovary tissue (graft). Furthermore, transplantation-induced activation as a mechanism of loss is likely the results of the graft preparation and transplantation process, which by necessity isolates the primordial follicles from the growing (antral, pre-antral and secondary) follicles that maintain the quiescence of the dormant follicles. The absence of growing follicles disrupts the balance between stimulatory and inhibitory follicle activation factors in the graft, thereby instigating follicular activation.

Hence, in certain example embodiments, one or more of the AMH receptor binding peptides described herein or functional fragments thereof can be administered, such as during the peri-transplant period, to preserve and prolong the function of the transplanted ovarian cortex. Additionally or alternatively, by mimicking the effects of AMH in certain aspects, administration of one or more of the AMH receptor binding peptides described herein can be used to delay or avoid further transplantation surgeries (currently, multiple surgeries are needed for the woman to achieve pregnancy and complete her family). In certain example embodiments, administration one or more of the AMH receptor binding peptides described herein during and/or post transplantation can restore the normal levels of AMH inhibition, thus preventing the mass follicle activation and loss that would otherwise occur, while preserving the PMF population of the graft. Advantageously, by preventing transplantation-induced follicle activation, it is believed that administration of one or more of the AMH receptor binding peptides described herein can improve tissue cryopreservation and transplantation clinical outcomes, improve the long-term graft endocrine activity, and increases fertility potential.

In certain example embodiments, co-administration of estrogen and/or progesterone hormones, such as an estrogen-containing contraceptive, can be used along with administration of one or more of the AMH receptor binding peptides. Such hormone administration is useful, for example, to prevent menopausal symptoms (hot flashes, moodiness, depression, osteoporosis) that may arise when administering the AMH receptor binding peptides described herein or functional fragments thereof. Patients that have non-functioning or reduced functioning ovaries are generally already supplemented with estrogen and/or progesterone hormones for the same reason. Following transplantation, administration of estrogen and/or progesterone can be used until the transplanted tissue begins to produce these hormones endogenously. Hence, in certain example embodiments, when one or more of the AMH receptor binding peptides are used in the context of ovarian cortex transplant as described herein, such administration can occur with or otherwise in addition to the administration of estrogen and/or progesterone (e.g., Lo-Estrin®, Kelnor®, or Yasmin®).

Endometriosis

In certain example embodiments, provided is a method for treating endometrioses. As those skilled in the art will appreciate, endometriosis is a benign but chronic disease in which endometrial tissue grows outside the uterus, such as in the ovaries, fallopian tubes, and/or the tissue lining the pelvis. This results in pain, adhesions, and decreased fertility in the afflicted subject. Further, the endometrium expresses the AMHR2 receptor with a functional AMH signal transduction system [30], thereby providing a potential therapeutic target for the one or more one or more of the AMH receptor binding peptides described herein or functional fragments thereof.

In certain example embodiments provided is a method for treating endometriosis, the method including administering to a subject one or more of the AMH receptor binding peptides described herein or functional fragments thereof. For example, and without being bound by any particular theory, it is believed that such administration of the one or more of the AMH receptor binding peptides described herein or functional fragments thereof can inhibit human endometrial stromal cells and increase their apoptosis, thereby treating the endometriosis. Additionally or alternatively, it is believed that administration of the one or more of the AMH receptor binding peptides described herein or functional fragments thereof can inhibits cell growth and induces autophagy, cell cycle arrest, and apoptosis. As such, administration of one or more of the AMH receptor binding peptides described herein or functional fragments thereof can be used to treat and/or ameliorate the symptoms of endometriosis.

Male Fertility Preservation

In certain example embodiments, provided is a method for preserving male fertility, the method including the administration of one or more of the AMH receptor binding peptides described herein to the subject. That is, administration one or more of the AMH receptor binding peptides described herein or functional fragments thereof can be used to preserve fertility in the male. AMH in the male is produced by the Sertoli cells and its serum level is used to determine testicular function. While the mechanism has not yet been elucidated, AMH is known to regulate regulates sperm production. For example, total AMH in seminal plasma showed a positive association with sperm motility [17]. Furthermore, AMH in seminal plasma has been suggested as a predictive marker for recovery of sperm motility after cryopreservation in men with low sperm motility [18].

Without wishing to be bound by any particular theory or mechanism of action, it is believed that administration of one or more of the AMH receptor binding peptides described herein would have the same effects as the native AMH on sperm production and could thus have a role in male fertility preservation and contraception. For example, administration of one or more of the AMH receptor binding peptides described herein may regulate sperm motility and possibly even regulate sperm count and quality. Accordingly, in certain example embodiments provided is a method of providing male contraception, the method including administering to the male subject one or more of the AMH receptor binding peptides described herein of functional fragments thereof.

Cancer Treatment & Prevention

In certain example embodiments, one or more of the AMH receptor binding peptides described herein or functional fragments thereof can be administered to a subject to treat cancer in the subject. That is, without being limited by any particular theory, it is believed that—by mimicking the effects of AMF—one or more of the AMH receptor binding peptides described herein or functional fragments can be used to treat cancer in any way that AMH can be used to treat cancer. For example, as those skilled in the art will appreciate, different types of ovarian cancer cells express AMH receptors [10], thus providing a target for the AMH in ovarian cancer. And recombinant AMH may be used to treat ovarian cancer and ocular melanoma [13, 14].

Accordingly, in certain example embodiments, provided is a method of treating ovarian cancer in a subject, the method including administering to the subject an effective amount of one or more of the AMH receptor binding peptides described herein or functional fragments thereof. For example, in certain embodiments administration of one or more of the AMH receptor binding peptides described herein or functional fragments thereof can be used to stall cellular function and replication, such as to treat granulosa cell tumors (and possibly other cancers tumors), by mimicking the effects of AMH. And, in certain example embodiments, the AMH receptor binding peptides described herein or functional fragments thereof can be used to prevent and/or treat non-gonadal tumors, such as melanomas and in particular ocular melanoma. For example, in certain example embodiments provided is a method of treating ocular melanoma in a subject, the method including administering to the subject an effective amount of one or more of the AMH receptor binding peptides described herein or functional fragments thereof.

In certain example embodiments, provided is a method of treating a subject who is undergoing, or will undergo, a gonadotoxic treatment, such as chemotherapy. Such therapies are known, for example, to induce rapid or complete follicle depletion. As those killed in the art will appreciate, post-cancer-treatment "burnout" is a condition that occurs when cancer treatment kills currently developing follicles. The lack of pre-antral follicles results in greatly reduced AMH production. This low AMH level triggers a DOR-like condition as primordial follicles mature too quickly. Moreover, because the follicles mature too quickly, they do not produce enough AMH to slow the follicle maturation, creating a feedback loop. If not treated, this results in running out of primordial follicles as in DOR.

Accordingly, in certain example embodiments provided is a method of restoring a normal rate of primordial follicle maturation, the method including administering to the subject one or more of the AMH receptor binding peptides described herein or functional fragments thereof. Likewise, in certain example embodiments is a method of reinstating pre-antral follicles in a subject, the method including administering to the subject one or more of the AMH receptor binding peptides described herein or functional fragments thereof to the subject. In such example embodiments, administration of the one or more of the AMH receptor binding peptides described herein or functional fragments thereof can function to maintain physiological functions associated with AMH.

In certain example embodiments, the subject can be treated with the one or more of the AMH receptor binding peptides described herein or functional fragments thereof before initiation of the gonadotoxic treatment. Additionally or alternatively, in certain example embodiments the subject can be treated with the one or more of the AMH receptor binding peptides described herein or functional fragments thereof concurrent to the gonadotoxic treatment. Additionally or alternatively, in certain example embodiments, the subject can be treated with the one or more of the AMH receptor binding peptides described herein or functional fragments thereof after the conclusion of the gonadotoxic treatment.

In certain example embodiments, one or more of the AMH receptor binding peptides described herein or functional fragments thereof can be used to treat breast cancer. That is, in certain example embodiments provided is a method of treating breast cancer in a subject, the method including administering to the subject an effective amount of one or more of the AMH receptor binding peptides described herein or functional fragments thereof. Most breast cancers are produced by the synchronous effects of estrogen and progesterone on the mammary gland. By halting hormonal production by the ovary, administration one or more of the AMH receptor binding peptides described herein can prevent the development, or progression, of breast cancer. For example, Tamoxifen, GnRH Agonists (e.g., Lupron® or Goserelin®) Anastrazole and Letrozole (Femara®), used as adjuvant therapy for the long-term treatment of receptor-positive breast cancer, can inhibit ovarian production of estrogen/progesterone to prevent cancer relapse. However, these compounds only inhibit ovulation. The AMH receptor binding peptides described herein would provide a more profound ovarian suppression by inhibiting the first step of folliculogenesis, rather than just ovulation, and would provide preservation of the ovarian follicles at the same time.

In certain example embodiments, one or more of the AMH receptor binding peptides described herein or functional fragments thereof can be administered alone to a subject to treat cancer, such as breast or ovarian cancer. In other example embodiments, the one or more of the AMH receptor binding peptides described herein or functional fragments thereof can be co-administered with a DNA damaging agent, a synthetic lethality agent (e.g., a PARP inhibitor), radiation, or a combination thereof. Examples of DNA damaging agents include, for example, platinum-based chemotherapy drugs (e.g., cisplatin, carboplatin, oxaliplatin, and picoplatin), anthracyclines (e.g., epirubicin and doxorubicin), topoisomerase I inhibitors (e.g., camptothecin, topotecan, and irinotecan), DNA crosslinkers such as mitomycin C, and triazene compounds (e.g., dacarbazine and temozolomide). Examples of synthetic lethality agents include, without limitation, PARP inhibitors or double strand break repair inhibitors in homologous repair-deficient tumor cells, PARP inhibitors in PTEN-deficient tumor cells, methotrexate in MSH2-deficient tumor cells, etc. Examples of PARP inhibitors include, without limitation, olaparib, iniparib, and veliparib. Examples of double strand break repair inhibitors include, without limitation, KU55933 (ATM inhibitor) and NU7441 (DNA-PKcs inhibitor). Additionally or alternatively, one or more of the AMH receptor binding peptides described herein can be used in conjunction with and/or co-administered with a taxane agent (e.g., doxetaxel, paclitaxel, abraxane), a growth factor or growth factor receptor inhibitor (e.g., erlotinib, gefitinib, lapatinib, sunitinib, bevacizumab, cetuximab, trastuzumab, panitumumab), and/or an antimetabolite (e.g., 5-flourouracil, methotrexate).

In certain example embodiments, one or more of the AMH receptor binding peptides described herein can be conjugated or otherwise joined to an anti-cancer drug or agent and thereafter used to target a cancer cell expressing an AMH receptor, such as AMHRII. In such example embodiment, the method can include conjugating or otherwise joining an anti-cancer to one or more of the AMH receptor binding peptides described herein, determining whether a subject suffering from a cancer has a cancer tumor cell that expressing the AMH tumor, and then administering the AMH receptor binding peptide-conjugate to the subject to treat the cancer. Such methods are described, for example, in U.S. Patent Publication 20190367625, which is hereby expressly incorporated herein in its entirety. Indeed, as will be appreciated by the present disclosure, one or more of the AMH receptor binding peptides described herein could be used according to the methods of U.S. Patent Publication 20190367625 to treat a variety of cancers, including colon cancer, liver cancer, hepatocellular carcinoma, testis cancer, thyroid cancer, gastric cancer, gastrointestinal cancer, bladder cancer, pancreatic cancer, head and neck cancer, kidney cancer, liposarcoma, fibrosarcoma, pleuramesothelioma, melanoma, sarcoma, brain cancer, osteocarcinoma, breast cancer, prostate cancer, leukemia, or any other cancer that expresses an AMH receptor and that hence would be responsive to a cancer treatment with an AMHR binding agent.

In certain example embodiments, the methods of treating cancer described herein may be cell and/or tissue specific. That is, one or more of the peptides described herein may beneficially target a specific cancer cell type while posing little or no cytotoxic effects to other cell types. For example, one or more of the peptides described herein or functional fragment thereof may target ovarian cancer tumors while posing little to no cytotoxic effects to non-tumor cells, such as non-tumorigenic granulosa cells. As such, the one or more peptides or functional fragments thereof described herein can be administered to a subject to target a specific cell type. Additionally or alternatively, the dose of the one or more peptides or functional fragments thereof described herein can be adjusted to as to decrease toxicity of non-tumor cells, such as granulosa cells.

AMH Binding Peptides as AMH Receptor Antagonists

In certain example embodiments, one or more of the AMH receptor binding peptides or fragments thereof can function as an AMH receptor antagonist. That is, one or more of the AMH receptor binding peptides or fragments thereof can reduce or inhibit the activity AMH receptor, thereby operating as an AMH receptor antagonist. For example, and without being bound by any particular theory, it is believed that the AMH receptor binding peptide or fragment thereof may compete with binding of endogenous AMH to the AMH receptor, thereby reducing the effects of endogenous AMH. That is, such antagonistic peptides are believed to bind to and occupy the AMH receptor, such as AMHR2, thereby preventing or reducing endogenous AMH from binding to the receptor. In such example embodiments, the one or more of the AMH receptor binding peptides or fragments thereof is believed to bind the receptor but not activate the receptor.

In embodiments where the one or more of the AMH receptor binding peptides or fragments thereof operate as an AMR receptor antagonist, such peptides can be used for any purpose in which inhibiting the function of endogenous AMH is desired. That is, one or more of the AMH receptor binding peptides or fragments thereof can be used to reduce the effects of endogenous AMH. Hence, in certain embodiments provided is a method for inhibiting AMH in a subject, the method including administering to the subject one or more of the AMH receptor binding peptides described herein or fragments thereof. Also provided, for example, is a method for treating a subject with elevated AMH levels, the method including administering to the subject one or more of the AMH receptor binding peptides described herein or fragments thereof.

In certain example embodiments, provided is a method for promoting the recruitment of primordial follicles into the pool of growing follicles in a subject, the method including administering to the subject one or more of the AMH receptor binding peptides or fragments thereof. As such, one or more of the AMH receptor binding peptides or fragments thereof can be used to treat fertility in a subject, such as the treatment of decreased ovarian reserve caused by a diminished number of primordial follicles that can be recruited into the pool of growing follicles and/or to promote fertility. In such example embodiments, administration of one or more of the AMH receptor binding peptides or fragments thereof can be combined with other hormone therapies, such as the co-administration of a fertility hormone, like FSH or LH.

In certain example embodiments, provided is a method for treating polycystic ovary syndrome (PCOS). As those skilled in the art will appreciate, PCOS is a condition in which the ovaries accumulate tiny "cysts" or small follicles (two to five millimeters in diameter, each of which contains an egg) instead of the follicles growing and proceeding to ovulation. Additionally, the stalled follicles secrete male hormone into the blood, causing hirsutism and with ovulation being rare without intervention. PCOS is thus recognized as one of the main causes of female infertility. Further, women who conceive with PCOS have higher incidences of premature delivery, gestational diabetes, high blood pressure, and even miscarriages.

As those skilled in the art will also appreciate, high AMH levels are a typical finding in PCOS, with such high levels increasingly being recognized as a biomarker for the syndrome [30]. The elevated AMH levels appear to suppress FSH-dependent maturation of antral follicles, thereby preventing selection and emergence of a dominant follicle. Conventional approaches address this suppression by either destroying the pre-antral and antral follicle pool, thereby lowering AMH levels or by raising serum FSH levels—the latter of which can be accomplished via the administration of gonadotropins, or indirectly, with selective estrogen receptor modulators and aromatase inhibitors [30]. These approaches, however, are not without deleterious side effects and complications [30].

Accordingly, in certain example embodiments provided is a method for treating PCOS, the method including administering to a subject one or more of the AMH receptor binding peptides described herein or fragments thereof, the AMH receptor binding peptide acting as an AMH receptor antagonist. Without being bound by any particular theory, it is believed, for example, that administration of the one or more of the AMH receptor binding peptides described herein or fragments thereof, functioning as an antagonist, can bind to AMH receptors in the subject, such as AMHR2, without activating the receptor. Such binding, however, prevents (blocks) endogenous AMH from binding to the receptor. Hence, the collective blocking of endogenous AMH-receptor binding reduces the effects of high endogenous AMH in the subject, thereby treating the subject.

EXAMPLES

The following examples further illustrate the invention but should not be construed as in any way limiting its scope. Considering the present disclosure and the general level of skill in the art, those of skill will appreciate that the following Examples are intended to be exemplary only and that numerous changes, modifications, and alterations can be employed without departing from the scope of the presently disclosed subject matter.

Example 1—Identification & Generation of AMH Receptor Binding Peptides

Ovarian aging determines follicular depletion and is quantified by decreasing Anti-Mullerian hormone (AMH) and increasing follicular stimulating hormone (FSH). AMH is believed to exert an inhibitory role in the recruitment and development of primordial follicles into developing follicles. In fact, in engineered AMH-null mice, the ovaries contain almost three-fold greater number of growing secondary follicles and a decreased number of primordial follicles [1]. This holds true for both the pre-pubertal and post-pubertal mice, and indicates that in the absence of AMH, primordial follicles are recruited at a faster pace. Further, it has been seen that in granulosa cell cultures AMH attenuates the FSH-dependent increase in aromatase activity and LH (luteinizing hormone) receptor expression, thus inhibiting FSH-dependent follicular growth [2]. Thus, AMH seems to downregulate two important steps of follicular development: follicle recruitment and cyclic selection for dominance [1, 3]. Mouse studies have shown that AMH serum levels reflect the size of the primordial follicle pool and its reduction with aging [4, 5].

In addition, human studies have shown that AMH directly correlates with the number of antral follicles assessed by ultrasound [6] and FSH, inhibin-B and estradiol [7]. AMH is a member of the transforming growth factor-beta gene family. Its expression is restricted in the male to the Sertoli cells of fetal and postnatal testis, and in the female to the granulosa cells of the ovary. Its production starts at the stage of primary follicles, soon after the columnar differentiation from the flat granulosa cells of primordial follicles [1]. Production of AMH is maximum in secondary follicles, gradually decreases in early tertiary follicles, and is nil in antral tertiary follicles, when the follicles are primarily under FSH control. Its action is mediated by several receptors, but the best known is AMH-R2 (or AMH Receptor 2).

In view of the several actions of AMH, and because of the need for AMH receptor agonists and/or antagonist that can modify the activity of one or more of the AMH receptors, provided herein are AMH receptor binding peptides that modulate the activity of the AMH receptor, as described herein. Briefly, it was hypothesized that peptides that bind AMH receptors could be generated based on the amino acid sequence of the AMH biding site of the AMH-R2 receptor. More particularly, based on the amino acid sequence of the AMH-R2 that is responsible for binding AMH, as well as the amino acid sequences of AMH-R2 that are near the AMH binding site, a peptide microarray was used to identify candidate AMH receptor binding peptides that can activate AMH-R2 and thus produce similar effects to native AMH.

Microarray Assay

To identify candidate AMH receptor binding peptides described herein, a custom peptide library composed of replicate copies of a 124,000 17mer peptide microarray was synthesized (Arizona State University, Tempe, Ariz.) using the method described in Legutki, J. B., et al., Scalable high-density peptide arrays for comprehensive health monitoring. *Nat Commun.*, volume 5, 4785 (2014). The slide was assembled into an Arrayit 4×24 Hybridization Cassette and each peptide microarray was blocked with 150 uL of 30% human sera in 1×PBST for 1 hour at room temperature with shaking. After blocking, the slide was washed 3× with 1×PBST using a Biotek plate washer prior to addition of protein targets. Each protein sample was diluted in 30% human sera in 1×PBST and 150 uL of each sample was dispensed into the appropriate wells in the cassette and incubated for 1 hour at 37 C with rotation at 300 rpm on a ThermoMix™ 500 heater/shaker.

After incubation, the cassette was dismantled, the slide washed 3 times in 1×PBST, rinsed three times with distilled, deionized water (ddH$_2$O), and dried in a centrifuge for 2 minutes at 800 rpm. Secondary antibody (anti-GST, GE Healthcare™) was prepared at 10 nM in 30% human sera in 1×PBST and dispensed onto the slide. The slide was incubated for 1 hour at 37 C with rotation at 300 rpm as before. The slide was then washed 3 times in 1×PBST, rinsed 3 times with ddH$_2$O, and dried in a centrifuge for 2 minutes at 800 rpm. Detection antibody, 10 nM Alexa Flour 647 donkey anti-goat IgG (H+L) (ThermoFisher Scientific™) was prepared in 0.75% casein in 1×PBST and dispensed onto the slide. The slide was covered and incubated for 1 hour at 37 C with rotation as before. The slide was washed 3 times in 1×PBST, rinsed 3 times with ddH$_2$O, and dried in a centrifuge for 2 minutes at 800 rpm. The slide was scanned on an Innopsys™ Inoscan 910AL scanner and the resulting TIFF files were analyzed using the Genepix™ Pro 6.0 software. Data files were exported and analyzed using Microsoft Excel™ and JMP™ software.

Peptide Identification & Generation

Based on the microarray analysis, 20 different candidate AMH receptor binding (SEQ ID NOS:1-20) were identified. These AMH receptor binding peptides, which are provided in Table 1 (above) as SEQ ID NOS: 1-20, have high affinity for the receptor and, for example, include some D-amino acid stereoisomers (Tryptophan; Leucine; Arginine; Alanine). While such D-amino acids are not expected to be needed for AMH receptor binding and activation, the D-amino acids are likely to confer higher stability against enzymatic degradation of the AMH receptor binding peptides, thus enhancing the durability of the peptides as biomaterials.

For generation of the peptides, the sequences of four of the peptides (SEQ ID NOS:1-4) to were submitted to Watsonbio Sciences (Watsonbio Sciences™, 7505 Fannin Street Suite 313, Houston, Tex. 77054) to be produced in powder form for use in the cell proliferation experiments described below (Example 2). Before their use in the cell proliferation assay below, the powder-form of the peptides (peptides corresponding to SEQ ID NOS:1-4) were reconstituted with Phosphate Buffered Saline (HyClone™). The peptides were then dissolved in PBS (HyClone™) at a concentration of 4 mg in 400 µl, stock concentration 10000 µg/ml.

Example 2—AMH Receptor Binding Peptides Reduce Cancer Cell Proliferation In Vitro This example describes the effect of the AMH receptor binding peptides from Example 1 on cellular proliferation, in accordance with certain example embodiments. Briefly, the first two AMH receptor binding peptides (SEQ ID NOS:1-2) from Table 1 were tested on four types of AMHR2-expressing, immortalized, chemotherapy-resistant ovarian cancer cells: SKOV-3 (ovarian serous cystadenocarcinoma), EL-1 (epithelial ovarian cancer), A2780 (endometroid ovarian cancer), and MDAH (endometroid ovarian cancer) in an MTT Assay (Trevigen™ MTT Cell Proliferation Assay).

MTT Assay

For each cell line, cells were seeded into Falcon tissue culture treated 96-well plates in a fixed volume of 100 mcl at a density of 8,000 cells/well. Three different doses (5 µg/ml, 10 µg/ml, and 20 µg/ml) of each AMH receptor binding peptide (i.e., AMHR2BP (SEQ ID NO: 1) or AMHR2BP2 (SEQ ID NO: 2)) were tested, along with a negative control peptide NegAMHR2BP (SEQ ID NO: 4) and an untreated (PBS) group. Each experiment was executed in triplicates. For 3+1 treatments×3 wells+10 extra=22 wells×8000 cells per well, the total number of cells needed per AMH receptor binding peptide/cell line was 176,000. The cells were spun down in a sterile 15 ml conical tube for 5 minutes at 200×g and then resuspended in 2.2 ml of media (100 ul per well×22 wells). 100 mcl of the cell-containing fluid (=8,000 cells) were placed in each well of the 96-well plate. After 24 hours the media was removed from each well and replaced with the 4 treatment media (phenol-free media). At this point, 10 extra wells with media, but no cells, were created per each cell line (10×4=40 wells). The AMH receptor binding peptides (AMHR2BP (SEQ ID NO: 1) or AMHR2BP2 (SEQ ID NO: 2)) were administered in the culture medium and the effects analyzed after 24 hours in culture as percentage reduction of cell replication using an MTT real-time RT-PCR assay.

Results

Figure 1B:
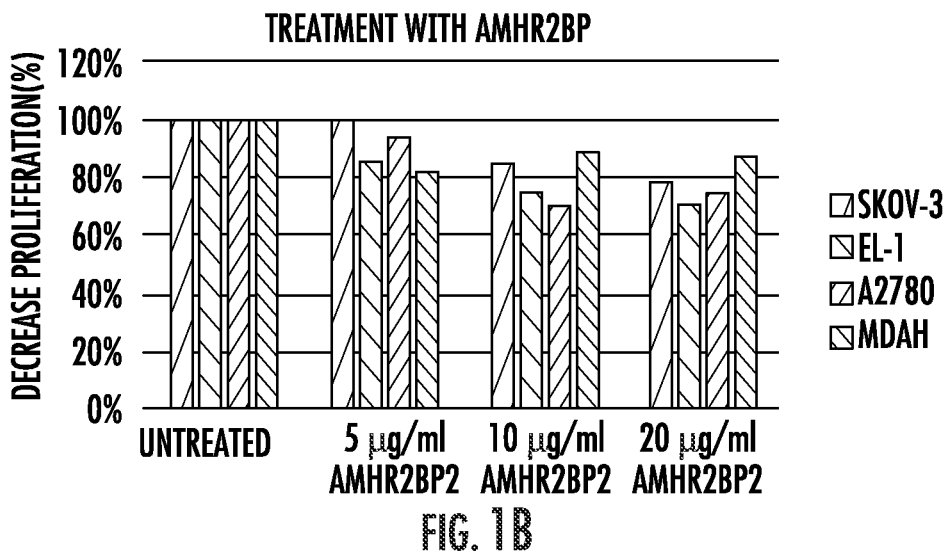
FIG. 1B is graph showing the effects of the peptide of AMHR2BP2 (SEQ ID NO: 2) on cellular replication in various cancer lines, in accordance with certain example embodiments. As shown, treatment of SKOV-3 (ovarian serous cystadenocarcinoma), EL-1 (epithelial ovarian cancer), A2780 (endometroid ovarian cancer), and MDAH (endometroid ovarian cancer) cells with 5 µg/ml, 10 µg/ml, and 20 µg/ml of AMHRBP2 (SEQ ID NO: 2) resulted in decreased cell proliferation as compared to untreated, control cells, especially at higher concentrations.
Figure 1C:
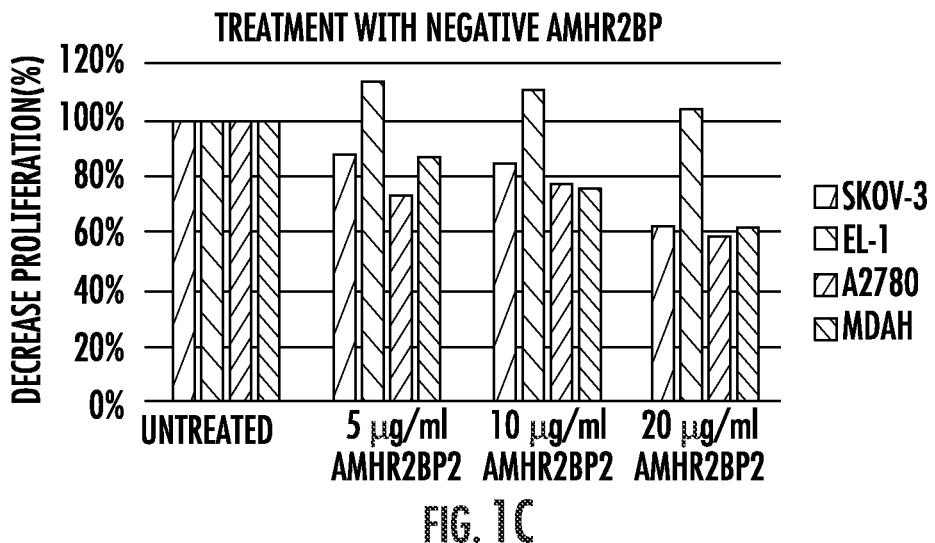
FIG. 1C is a graph showing the effects of NegAMHR2BP (SEQ ID NO: 4) on cellular replication in various cancer lines, in accordance with certain example embodiments. As shown, NegAMHR2BP (SEQ ID NO: 4) decreased proliferation in SKOV-3 (ovarian serous cystadenocarcinoma) cells, A2780 (endometroid ovarian cancer) cells, and MDAH (endometroid ovarian cancer) cells, while EL-1 (epithelial ovarian cancer) cell proliferation was slightly elevated at lower doses.

As shown in FIG. 1A, AMHR2BP (SEQ ID NO: 1) was able to fully stop cellular proliferation at concentrations 10 µg/ml in SKOV-3, EL-1, and A2780 cells lines, while a concentration of 20 µg/ml of AMHR2BP (SEQ ID NO: 1) arrested cell proliferation in all cell lines tested, as compared to control (untreated) cells. Indeed, while progressive proliferation reduction was noted at concentrations 5 µg/ml, 10 µg/ml for AMHR2BP (SEQ ID NO: 1), the reduction became absolute at 20 µg/ml (FIG. 1A). As shown in FIG. 1B, AMHR2BP2 (SEQ ID NO: 2) also reduced cellular proliferation, as compared to the control (untreated), though this reduction was less pronounced than for treatments with AMHR2BP (SEQ ID NO: 1). As shown in FIG. 1C, treatment with the negative peptide NegAMHR2BP (SEQ ID NO: 4) had little effect on cell proliferation at low concentration, while higher concentrations (10 and 20 µg/ml) decreased proliferation in SKOV-3 (ovarian serous cystadenocarcinoma) cells, A2780 (endometroid ovarian cancer) cells, and MDAH (endometroid ovarian cancer) cells. EL-1 (epithelial ovarian cancer) cell proliferation was slightly elevated at lower doses for the NegAMHR2BP (SEQ ID NO: 4). The control (untreated) ovarian cancer cells did not show any reduction in cell proliferation (FIG. 1A, FIG. 1B, and FIG. 1C).

Example 3—In Vitro Effect of AMH Receptor Binding Peptides on AMH-Pathway Markers and Granulosa Cell Proliferation In the female, anti-Müllerian hormone (AMH) is secreted by the granulosa cells (GCs) and its primary action is paracrine on other GCs, within the ovarian cortex. AMH precludes primordial follicles from progressing to primary follicles and regulates recruitment of the dominant follicle during the follicular phase of the menstrual cycle [1, 19]. By binding to its receptor AMH-R2 on GCs, AMH also influences other transcription factors and regulates gene transcription of other cytokines [20, 21]. Encoded in chromosome 12q13.13, AMH-R2 is a transmembrane serine/threonine kinase receptor which activates SMAD transcriptional regulators. In the ovary, AMH-R2 is localized on GCs and thecal cells, while it is not found on the oocyte [22].

Previous observations have confirmed the inhibitory role of AMH on ovarian cortex [23]. The inhibitory role of AMH has also been characterized in several in vitro and in vivo studies. In fact, recombinant AMH (rAMH) was found to reduce tissue expression of the hormones AMH and inhibin B, and to downregulate expression of hormone receptors AMHR2, FSH-R, LH-R, IGF1-R1 in in vitro human ovarian cortex [24]. RAMH also caused down-regulation of the sternness markers Octamer-binding transcription factor-4 (Oct-4), SRY (sex determining region Y)-box 2 (Sox2), and homeobox protein NANOG (NANOG), in fresh and vitrified/thawed ovarian cortex [11]. Furthermore, it has been demonstrated that rAMH could inhibit follicle pre-activation and burn out after xenotransplantation of human ovarian cortex into nude mice, where it was observed that rAMH caused preservation of primordial follicles and ovarian cortex hormone production, precluding initiation of the development into primary and secondary follicles [9]. These findings corroborated the results of a study on luteinized GCs, where rAMH was shown to directly inhibit stem cell factor expression [25]. Those outcomes have been subsequently strengthened by establishing that, in luteinized GCs, rAMH significantly reduced cellular expression of AMH, AMH-R2, FSH-R and Inhibin B (greater than 50% reduction in the rAMH group, compared to the control group) and cell proliferation and apoptosis (Ki67 and Caspase3 were reduced greater than 30% in the rAMH group) [26].

In this example, the affinity of AMHR2BP (SEQ ID NO: 1) for AMH-R2 was investigated by performing an in vitro study on luteinized GCs. More particularly, this example examined whether the peptide of SEQ ID NO: 1 from Example 1 (above) was able to reduce hormonal production and decrease cellular proliferation/apoptosis, similar to the effects of native AMH. The hypothesis was that AMHR2BP (SEQ ID NO: 1) could reproduce the same effects of native AMH in all cells/tissues where the receptor AMH-R2 is present.

GCs Primary Culture

GCs were isolated at the time of oocyte retrieval from three IVF/ICSI patients with tubal factor infertility as previously reported [26]. Follicular aspirates were centrifuged at 900×g at room temperature. Blood contaminants were removed from GCs by Histopaque™ 1077 (Sigma-Aldrich™, St. Louis, Mo., USA) gradient centrifugation at 800×g for 20 min at room temperature. The GC pellet was resuspended in a 20-ml volume of medium [Dulbecco's modified Eagle's medium/Ham's Nutrient Mixture F-12 (Gibco, Thermo Fisher Scientific, Inc., Waltham, Mass., USA) with 10% fetal bovine serum (make) and washed by a further 10-min centrifugation at 500×g. The GC pellet was then resuspended in 1 ml GC preparation medium containing 0.02% (w/v) EDTA and gentle repeated pipetting was performed to break up any cellular clumps. Following further washing, the cell stock was resuspended in the GC culture medium. The cells were seeded in nine-well cell culture plates at a density of 100,000 cells/well in medium and incubated for 24 hours with PBS (control), the NegAMHR2BP (SEQ ID NO: 4), or AMHR2BP (SEQ ID NO: 1).

Treatment

For determination of cytotoxicity of the novel AMHR2BP (SEQ ID NO: 1), a Cell Counting Kit-8 (CCK-8) proliferation and cytotoxicity assay was used. CCK-8 is a as a sensitive colorimetric assay where Dojindo's highly water-soluble tetrazolium salt is reduced by dehydrogenase activities in cells. Living cells reduce the salt, producing a yellow-color formazan dye, which is soluble in the culture media. The amount of dye, generated by the activities of dehydrogenases in GCs, is directly proportional to the number of living cells. CCK-8 detection sensitivity is very high. We tested the following: (a) AMHR2BP (SEQ ID NO: 1) concentrations: 20 µg/ml, 50 µg/ml, 80 µg/ml, in addition to (b) NegAMHR2BP (SEQ ID NO: 4) 80 µg/ml, and (c) untreated cells (control).

Following an overnight incubation (37° C., 5% $CO_2$), cells were treated with AMHR2BP 10 µg/ml (AMHR2BP group (SEQ ID NO: 1)), NegAMHR2BP (SEQ ID NO: 4) 10 µg/ml, or Phosphate-buffered saline (control group), for 24 hours. The AMHR2BP (SEQ ID NO: 1) dose was arbitrarily chosen based on extrapolation from the CCK-8 cytotoxicity assay. After incubation, we performed real-time RT-PCR to quantify GCs expression of AMH, AMH-R2, FSH-R, Inhibin B, cell proliferation (Ki67) and apoptosis (Caspase 3).

Real-Time RT-PCR Analysis

To determine cellular mRNA levels of AMH, AMH-R2, FSH-R, Inhibin B, Ki67, and caspase 3, we utilized real-time RT-PCR. The procedure has been previously published [9, 11, 24, 26, 27]. Briefly, total RNA was extracted from tissues with the RNeasy Mini Kit (Qiagen). GCs were first homogenized in lysis buffer provided in the kit and RNA extracted according to the protocol provided by the manufacturer. A 20-µl cDNA reaction volume using an equal amount of RNA (up to 1 µg) was prepared using the SuperScript™ VILO MasterMix Kit (Life Technologies™, Grand Island, N.Y.), as described by the manufacturer's protocol. Real-time RT-PCR was performed with the Express SYBR GreenER™ qPCR SuperMix RT-PCR kit (Life Technologies™) and a Cepheid 1.2f Detection System (Cepheid™, Sunnyvale, Calif.). Each 25-µL reaction included 12.5 µl of 2× QuantiTect™ SYBR Green RT-PCR master mix, cDNA template, and 0.2 µM each of target-specific primer were selected with the aid of the software program, Beacon Designer™ (Premier Biosoft™, Palo Alto, Calif.).

Oligonucleotide primers that amplify variable portions of the protein coding regions were established and verified and are described in Table 2. Standards with known concentrations were designed specifically for β-actin (79 base pairs (bp), AMH (102 bp), AMH-R2 (81 bp), FSH-R (97 bp), Inhibin B (104 bp), Ki67 (156 bp), and caspase 3 (170 bp) using the Beacon Designer™ software, allowing for construction of a standard curve using a tenfold dilution series. An individual standard for each gene of interest provides a method for absolute quantification of the gene in interest. The PCR reaction conditions were programmed as follows: an initial cycle was performed at 95° C. for 60 seconds. Next, there was 35 cycles of denaturation at 95° C. for 15 seconds, annealing time and temperatures as described in Table 2, followed by a final cycle at 72° C. for 30 seconds to allow completion of product synthesis. A melting curve analysis was performed to demonstrate the specificity of the PCR product as a single peak. A control, which contains all the reaction components except for the template, was included in all experiments.

Data are expressed as mean+standard deviation (SD). For comparisons between the three groups, we used ANOVA with Tukey's post-test analysis (SPSS v25, Chicago, Ill.). A p-value $<0.05$ indicated significance.

TABLE 2

Real-time RT-PCR oligonucleotide primer sequences and cycling conditions.

| Accession # | Gene | Sense (3'-5') | Antisense (5'-3') | Amp. Size (bp) | Ann'l. Temp. (° C.) | Ann'l. Time (sec) |
|---|---|---|---|---|---|---|
| NM_001101 | B-actin | ATGACTTAGTTGCG TTACAC (SEQ ID NO: 21) | AATAAAGCCATGC CAATCTC (SEQ ID NO: 22) | 79 | 58 | 10 |
| NM_000479 | AMH | GTGCTGCTGCTGAA GATG (SEQ ID NO: 23) | CTCCGACAGGCTG ATGAG (SEQ ID NO: 24) | 102 | 62 | 10 |
| NM_001164690 | AMH-R2 | CCAGAAGCACGGCT GACAG (SEQ ID NO: 25) | TGGAAAGGGGTGG CTCTCT (SEQ ID NO: 26) | 81 | 66 | 10 |
| NM_004346 | Caspase-3 | AGACATACTCCTTC CATCA (SEQ ID NO: 27) | ATCACTGTAACTT GCTAATCA (SEQ ID NO: 28) | 170 | 55 | 10 |
| NM_002417 | Ki67 | TCCTTTGGTGGGCA CCTAAGACCTG (SEQ ID NO: 29) | TGATGGTTGAGGC TGTTCCTTGATG (SEQ ID NO: 30) | 156 | 55 | 30 |
| AY429104 | FSH-R | GTCCACAACACCCA TCCAAGG (SEQ ID NO: 31) | GGGCTAAATGACT TAGAGGGACAA (SEQ ID NO: 32) | 97 | 66 | 10 |
| NM_002192 | Inhibin B | CCTGAAACTCCTGC CCTACG (SEQ ID NO: 33) | CCACCATGTTCCA CCTGTCA (SEQ ID NO: 34) | 104 | 66 | 30 |

Results

Figure 2:
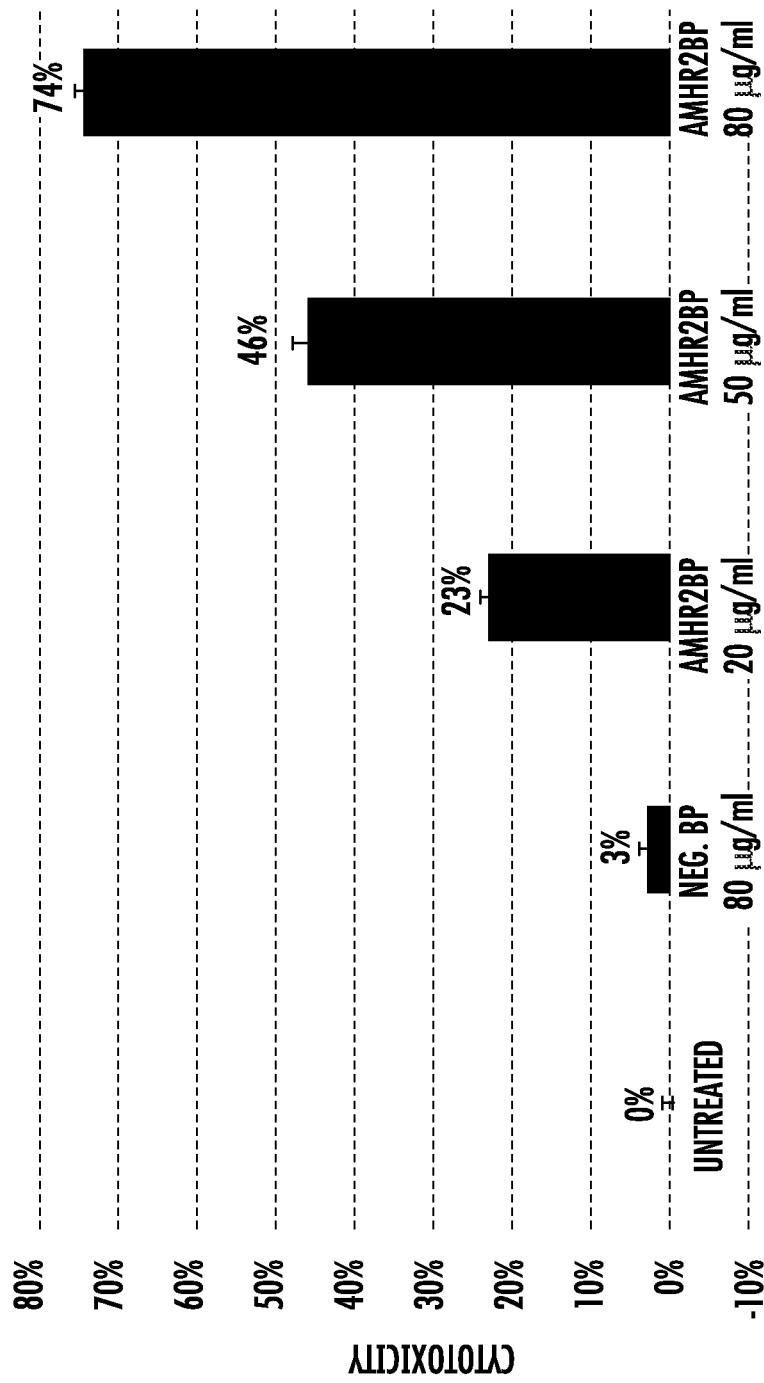
FIG. 2 is a graph showing a Cell Counting Kit-8 (CCK-8) proliferation and cytotoxicity assays for granulosa cells treated with increasing doses of the Anti-Müllerian hormone Receptor 2 binding peptide AMHR2BP (SEQ ID NO: 1), in accordance with certain example embodiments. No peptide was used for the control (untreated), while NegAMHR2BP (SEQ ID NO: 4) was used as the negative control (i.e., the Neg. BP, 80 µg/ml). As shown, for AMHR2BP (SEQ ID NO: 1), cytotoxicity is directly proportional to dose of the peptide AMHR2BP (SEQ ID NO: 1). Also, as shown, the negative peptide NegAMHR2BP (SEQ ID NO: 4) has low granulosa cell toxicity, even at 80 µg/ml.

The GCs primary culture was kept alive for 4 months. The results of the CCK-8 cytotoxicity assay for GCs treated with AMHR2BP (SEQ ID NO: 1) are reported in FIG. 2. As shown, there was a clear dose-effect: at the maximum concentration tested, 80 µg/ml, 74% of the GCs ceased function and were considered lifeless. At 20 µg/ml concentration AMHR2BP (SEQ ID NO: 1), 23% were considered lifeless. We thus chose the treatment dose of 10 µg/ml based on the cytotoxicity test results (FIG. 2). The NegAMHR2BP (SEQ ID NO: 4) had a low GC toxicity even at 80 µg/ml concentration.

Figure 3A:
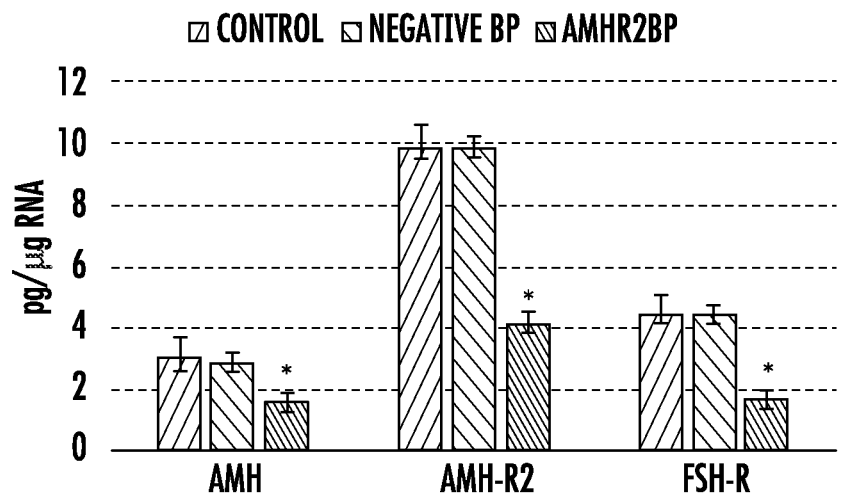
FIG. 3A is a graph showing expression of Anti-Müllerian Hormone (AMH), Anti-Müllerian Hormone Receptor 2 (AMH-R2), and the Follicular Stimulating Hormone Receptor (FSH-R), in granulosa cells treated with 10 µg/ml of the Anti-Müllerian hormone Receptor 2 binding peptide AMHR2BP (SEQ ID NO: 1), in accordance with certain example embodiments. As shown, granulosa cell expression of AMH, AMH-R2, and FSH-R each decreased in cells treated with AMHR2BP (SEQ ID NO: 1), as compared to the control (no peptide) and NegAMHR2BP (SEQ ID NO: 4) (*P≤0.005).
Figure 3B:
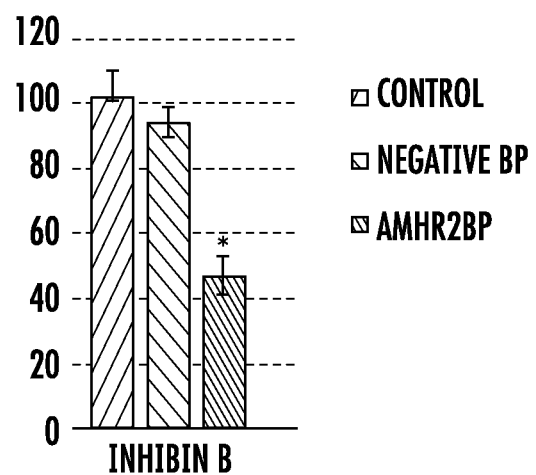
FIG. 3B is a graph showing expression of Inhibin B in granulosa cells treated with 10 µg/ml of the Anti-Müllerian hormone Receptor 2 binding peptide AMHR2BP (SEQ ID NO: 1), in accordance with certain example embodiments. As shown, granulosa cell expression of Inhibin B decreased in cells treated with AMHR2BP (SEQ ID NO: 1), as compared to the control (no peptide) and NegAMHR2BP (SEQ ID NO: 4) (*P≤0.005).
Figure 3C:
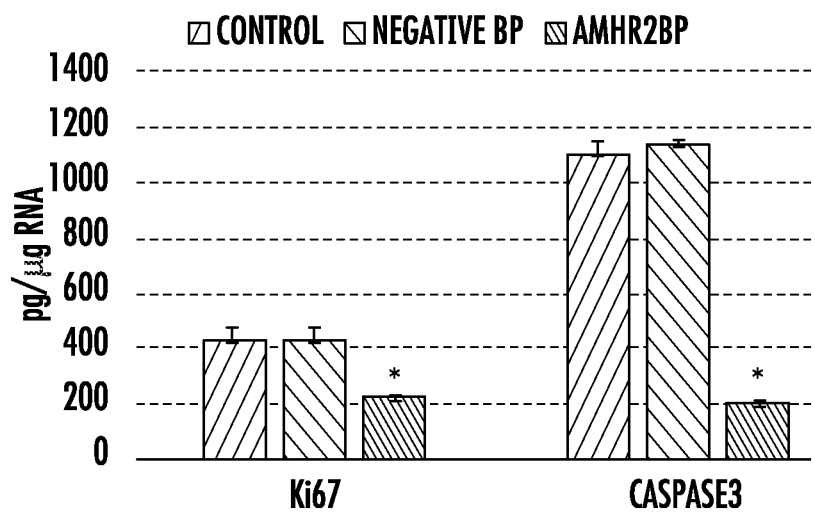
FIG. 3C is a graph showing expression of Ki67 (cell proliferation marker) and Caspase3 (apoptosis marker), in granulosa cells treated with 10 µg/ml of the Anti-Müllerian hormone Receptor 2 binding peptide AMHR2BP (SEQ ID NO: 1), in accordance with certain example embodiments. As shown, granulosa cell expression of Ki67 and Caspase3 each decreased in cells treated with AMHR2BP (SEQ ID NO: 1), as compared to the control (no peptide) and NegAMHR2BP (SEQ ID NO: 4) (*P≤0.005).

After incubation for 24 hours in 10 µg/ml of the AMHR2BP (SEQ ID NO: 1), cellular expression of AMH, AMH-R2, FSH-R (FIG. 3A) and Inhibin B (FIG. 3B), were significantly reduced compared to the NegAMHR2BP (SEQ ID NO: 4) peptide and control (no peptide) groups. In addition, GCs in the AMHR2BP (SEQ ID NO: 1) group showed decreased cell proliferation, as well as decreased apoptosis (FIG. 3C). Table 3 also shows the results of the quantitative PCR analysis. In fact, after incubation with the AMHR2BP (SEQ ID NO: 1) at 10 µg/ml, cellular expression of AMH-R2, FSH-R, Inhibin B, cell proliferation (Ki67), and apoptosis (caspase3), were significantly reduced by greater than 50%, while AMH was reduced by 45%.

TABLE 3

Quantitative PCR mRNA levels (±DS) for different variables in the three groups.

| Variable Groups | AMH pg/µg RNA | AMH-R2 pg/µg RNA | FSH-R pg/µg RNA | Inhibin B pg/µg RNA | Ki67 pg/µg RNA | Caspase3 pg/µg RNA |
|---|---|---|---|---|---|---|
| Control | 3.05 ± 0.1 | 9.88 ± 0.3 | 4.43 ± 0.3 | 101.8 ± 5.9 | 425.1 ± 16.6 | 1101.6 ± 91.4 |
| NegAMHR2BP (SEQ ID NO: 4) | 2.91 ± 0.2 | 9.95 ± 0.1 | 4.42 ± 0.4 | 94.0 ± 2.7 | 428.3 ± 6.8 | 1140.4 ± 16.8 |
| AMHR2BP (SEQ ID NO: 1) | 1.60 ± 0.1 | 4.17 ± 0.2 | 1.65 ± 0.1 | 46.9 ± 1.1 | 229.5 ± 6.7 | 207.3 ± 4.7 |
| % Change | −45% | −58% | −63% | −51% | −56% | −82% |
| p-value | <0.001 | <0.001 | <0.001 | <0.001 | <0.001 | <0.001 |

Discussion

This experiment showed that AMH receptor binding peptides, and in particular AMHR2BP (SEQ ID NO: 1), inhibited GCs' expression of AMH, AMH-R2, FSH-R and Inhibin B, in addition to significantly diminishing cell proliferation, as well as apoptosis. AMHR2BP (SEQ ID NO: 1) thus replicated the inhibitory effects of native AMH on luteinized GCs' function [26].

The inhibitory effect that AMH exerts on granulosa cells has multiple benefits on the ovary. Regulation of cyclic ovulation [1, 19] by various mechanisms [28], inhibition of tumor growth [14], and prevention of follicle burnout after ovarian tissue transplantation, or systemic chemotherapy [9, 29], comprise only a few of those benefits. We have confidence that most applications of AMH [11, 30] could be replaced with AMHR2BP (SEQ ID NO: 1) in the future. The advantages of using AMHR2BP (SEQ ID NO: 1) in place of recombinant AMH are multiple, encompassing a lower expense to reach therapeutic doses, avoidance the triggering of other undesired effects portrayed by the whole hormone (the peptide is specific for AMH-R2 receptor), the presence of D-amino acids, which allows for an enhanced stability and performance [31], to name a few.

Notably, the NegAMHR2BP (SEQ ID NO: 4) was shown to have low toxicity as compared to AMHR2BP (SEQ ID NO: 1) (FIG. 2). Nonetheless, the NegAMHR2BP (SEQ ID NO: 4) was shown to reduce proliferation of various ovarian cancer cells lines in a cell-specific manner (FIG. 1C). Hence, certain of the AMH receptor binding peptides described herein may have a cell or tissue specific effect. Such specific effects, i.e., low toxicity to normal cells (e.g., granulosa cells) with toxicity to specific cancer cells (e.g. SKOV-3 cells), indicates that the AMH receptor binding peptides described herein can be used as a well-tolerated cancer treatment or therapeutic.

Example 4—In Vivo Effect of AMH Receptor Binding Peptides on Follicle Count, Necroses, and Cell Proliferation AMH inhibits hormone production, and ovarian cortex follicle development in in vitro, and in vivo, ovarian cortex [9, 24], and in luteinized granulosa cells (GCs) [32]. As shown above, AMHR2BP (SEQ ID NO: 1), binding to AMH-R2, caused inhibition on GCs, in an in vitro. We thus sought to investigate whether the novel AMHR2-binding peptide AMHR2BP (SEQ ID NO: 1) could perform similarly to native AMH and control age-linked ovarian follicular reservoir in a mouse model. Hence, this example shows the effect of the AMH receptor binding peptides, and specifically AMHR2BP (SEQ ID NO: 1), on follicle count, necroses, and proliferation in an in vivo mouse model.

Mouse Treatment

Knowledge of the developmental landmarks and the highly inbred conformity made C57BL/6J female mice a natural choice for this study. In this mouse strain, puberty is characterized by vaginal opening at approximately 25 days of life, estrus 3-4 days later, and subsequently by regular cycling every 5-6 days. Maturity is considered to be reached at 90 days of life (12 weeks).

Briefly, 24 C57BL mature female mice (18 weeks old) were allocated to four (4) experimental groups: baseline group (6 mice), AMHR2BP (SEQ ID NO: 1) group (6 mice), a recombinant rAMH group (6 mice), and control group (6 mice; 21 weeks of age, that received saline). The six mice in the baseline group were euthanized at the beginning of the experiment and comprised the baseline against which to compare the 2 experimental, and the control, groups. Mice in the AMHR2BP (SEQ ID NO: 1) group received AMHR2BP (SEQ ID NO: 1) at a daily dose of 50 µg/day (BP group); the rAMH group received recombinant AMH (rAMH) at a daily dose of 1.8 µg/day (to obtain 24.0 µg/ml serum level), and the control group received normal saline.

Figure 4:
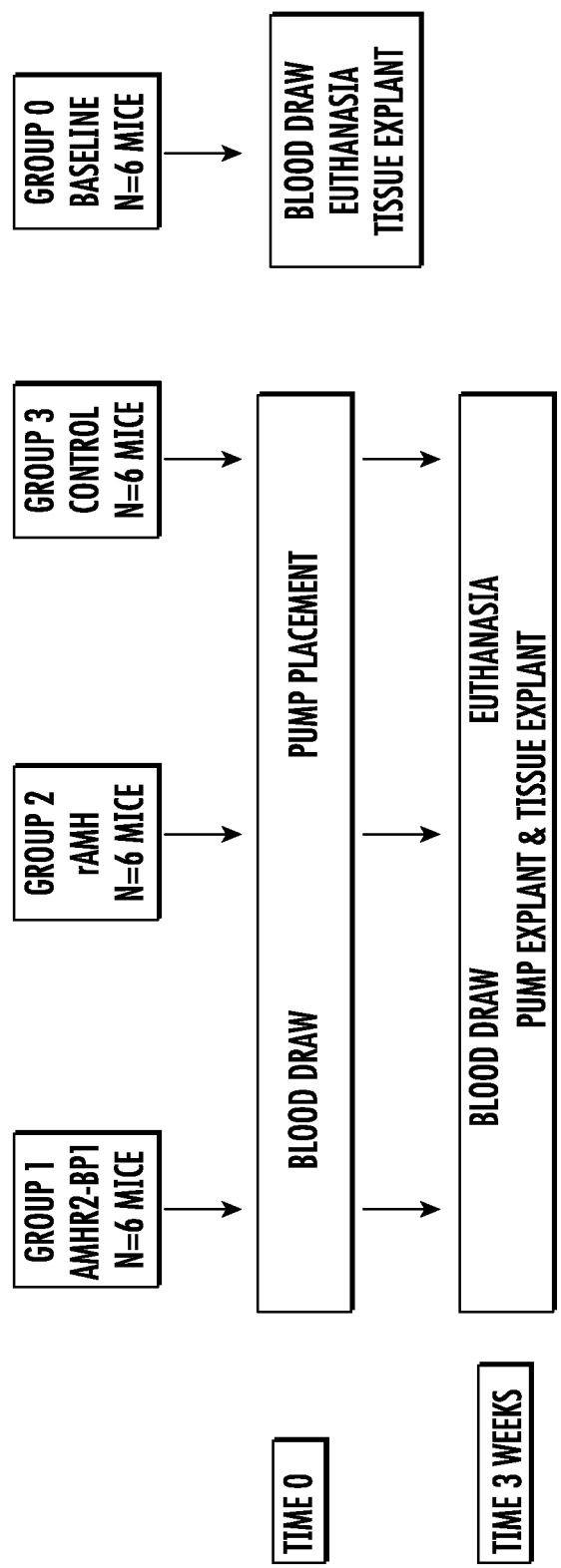
FIG. 4 is an illustration depicting the timeline of in vivo studies of the effects of AMHR2BP (SEQ ID NO: 1) on mouse ovary histology and granulosa cell proliferation, in accordance with certain example embodiments.
Figure 5A:
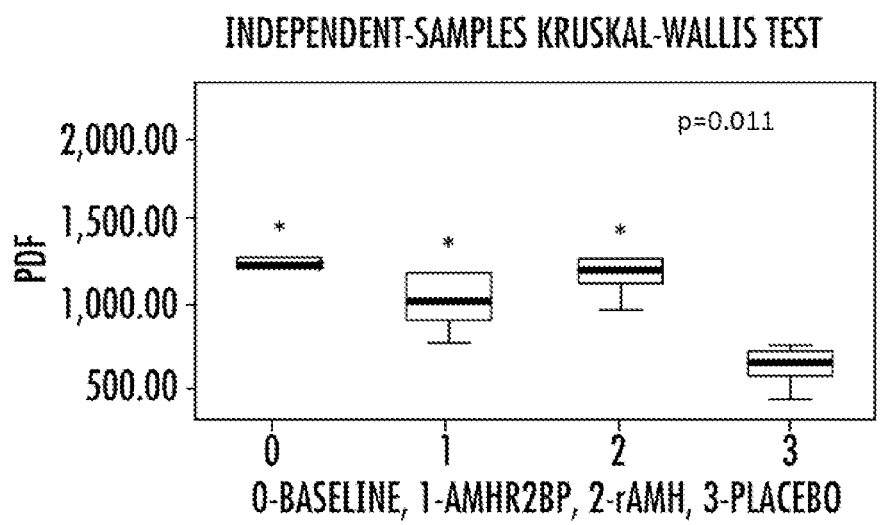
FIG. 5A is a graph showing the concentration of primordial follicles (PDF) per millimeter cube in the mouse ovaries after treatment with AMHR2BP (SEQ ID NO: 1), recombinant Anti-Müllerian hormone (rAMH), or placebo, in accordance with certain example embodiments. As shown, the concentration of PDFs decreased in the Placebo group, while it is maintained in mice treated with AMHR2BP (SEQ ID NO: 1) and rAMH (*P>0.005), similar to the number in the baseline group (younger age).
Figure 5B:
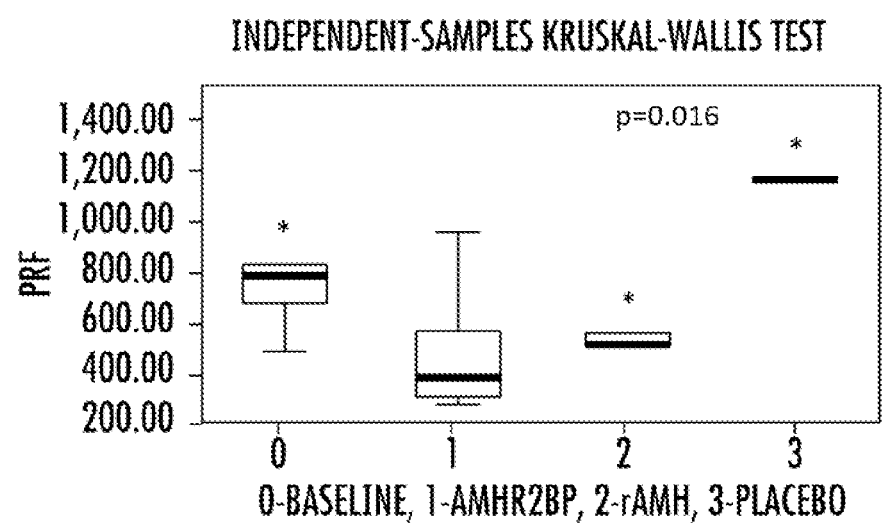
FIG. 5B is a graph showing the concentration of primary follicles (PRF) per millimeter cube in the mouse ovaries after treatment with AMHR2BP (SEQ ID NO: 1), recombinant Anti-Müllerian hormone (rAMH), or placebo, in accordance with certain example embodiments. As shown, the concentration of PRFs increased in the Placebo group, while it is low in mice treated with AMHR2BP (SEQ ID NO: 1) and rAMH (*P>0.005), similar to the number in the baseline group (younger age).
Figure 5C:
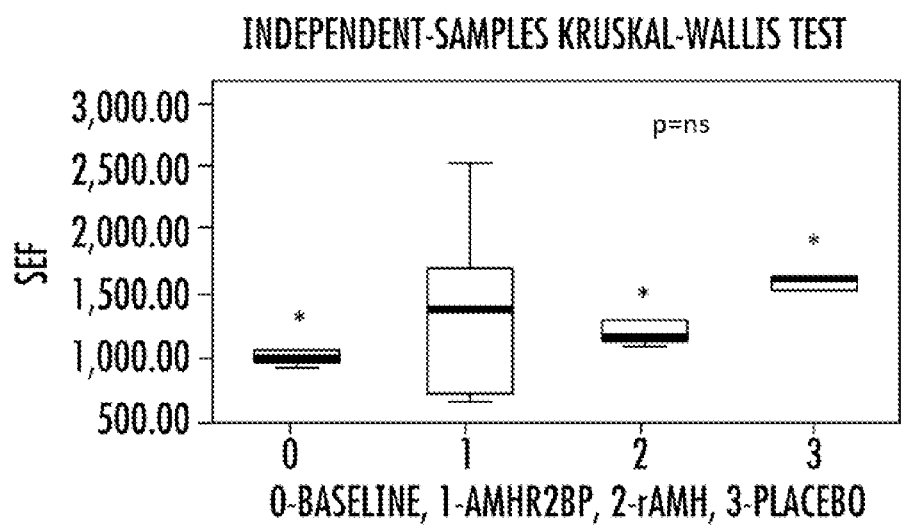
FIG. 5C is a graph showing the concentration of secondary follicles (SEF) per millimeter cube in the mouse ovaries after treatment with AMHR2BP (SEQ ID NO: 1), recombinant Anti-Müllerian hormone (rAMH), or placebo, in accordance with certain example embodiments. As shown, the concentration of SEFs increased in the Placebo group, while it is lower in mice treated with AMHR2BP (SEQ ID NO: 1) and rAMH (*P>0.005), similar to the number in the baseline group (younger age).
Figure 5D:
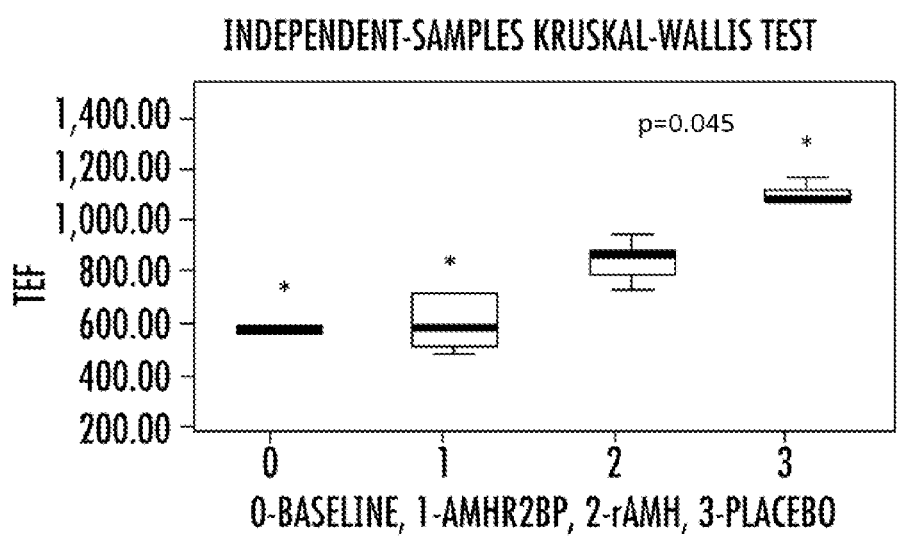
FIG. 5D is a graph showing the concentration of tertiary follicles (TEF) per millimeter cube in the mouse ovaries after treatment with AMHR2BP (SEQ ID NO: 1), recombinant Anti-Müllerian hormone (rAMH), or placebo, in accordance with certain example embodiments. As shown, the concentration of TEFs increased in the Placebo group, while it is lower in mice treated with rAMH, and even lower in mice treated with AMHR2BP (SEQ ID NO: 1) (*P>0.005), similar to the number in the baseline group (younger age).

In order to accomplish this task, an osmotic pump was implanted intraperitoneally at time zero. FIG. 4 shows a timeline of the experiment. The osmotic pump (ALZET Osmotic Pumps, model 1004, Cupertino, Calif.) administered AMHR2BP (SEQ ID NO: 1) and rAMH with a flow rate (QT) of 0.11 µl/h for 4 weeks, based on a mouse temperature of 36.9° C. and a tissue osmolality of 7.5 atm. The daily AMHR2BP (SEQ ID NO: 1) dose was chosen based on the results of Example 3 (above) and estimated in vitro to in vivo extrapolation (IVIVE), while the rAMH dose was determined as described in reference [26]. Mice in the control group were treated with normal saline by using the same osmotic pump vehicle implanted intraperitoneally. All mice in the 2 experimental, and the control, groups were euthanized 3 weeks into the experiment. All mice underwent a blood draw just prior to euthanasia, and their ovaries were explanted for real-time RT-PCR and histological analyses.

Mouse Ovarian Tissue Histological Procedures & Analysis

After dissection, one ovary was stored in formalin and embedded in paraffin for immunohistochemical examination of follicular development and count with hematoxylin and eosin staining, while Ki67 slides were used for examination of cell proliferation. The other ovary was frozen for mRNA analysis (see below). Five µm-thick sections were serially cut and every 5th section analyzed for follicular counts. All ovarian cortex specimens where obtained from each group, and at least three sections were analyzed in each tissue specimen. The computerized program used for image analysis, CaseCenter™ by 3DHistech Pathology Information System™ (Version 2.3; Budapest, Hungary), allowed us to examine all the sections at the same time and to accurately count all the follicles in each section without redundancy. For follicle counting, the investigators were blinded to the treatment groups. One oocyte surrounded by a monolayer of flat, or cubic, granulosa cells enclosed by a basement membrane identified a primordial (PDF) and a primary follicle (PRF), respectively. Secondary follicles (SEF) were identified with one oocyte surrounded by multiple layers of cubic granulosa cells, and tertiary follicles (TEF) by fluid accumulation amid the granulosa cells.

Results

No mouse deaths or obvious toxicity were noted in any of the in vivo studies. When compared with the baseline group (18 weeks' age), the AMHR2BP (SEQ ID NO: 1) group exhibited increased SEFs, and decreased PRFs, while the number of PDFs, TEFs, and corpora lutea did not change. When compared with the control group (21 weeks' age), the AMHR2BP (SEQ ID NO: 1) group exhibited increased PDFs and corpora lutea, while PRFs, and TEFs were significantly decreased, and SEFs were unchanged. These data are provided in Table 4 (below). AMHR2BP (SEQ ID NO: 1) caused decreased cell proliferation in the secondary follicles. Accordingly, AMHR2BP (SEQ ID NO: 1) treatment for 3 weeks (equivalent to 3 menstrual cycles in the BLC67 mouse) caused downregulation of follicular development and preservation of the ovarian follicle reserve. The increased number of SEF was likely due to extension of follicle life by AMHR2BP (SEQ ID NO: 1). Accordingly, AMHR2BP (SEQ ID NO: 1) could be used to inhibit age-linked loss of ovarian follicle reserve.

TABLE 4

Ovarian cortex concentration of follicles (PDF, PRF, SEF, and TRF)
in baseline, Placebo, rAMH, and AMHR2BP (SEQ ID NO: 1) groups.

| Variable | Baseline Median (Q1, Q3) | Placebo Group Median (Q1, Q3) | rAMH Group Median (Q1, Q3) | AMHR2BP (SEQ ID NO: 1) Group Median (Q1, Q3) | p-value* |
|---|---|---|---|---|---|
| PDF/mm$^3$ | 1195 (1191, 1248) | 614 (538, 705) | 1182 (1095, 1248) | 1012 (916, 1134) | 0.011 |
| PRF/mm$^3$ | 788 (670, 817) | 1165 (1152, 1176) | 514 (497, 548) | 383 (306, 533) | 0.016 |
| SEF/mm$^3$ | 970 (968, 1061) | 1613 (1528, 1664) | 1144 (1119, 1300) | 1371 (852, 1662) | ns |
| TEF/mm$^3$ | 583 (579, 606) | 1082 (1076, 1119) | 871 (808, 890) | 587 (519, 707) | 0.045 |
| Corp. Lutea/mm$^3$ | 6.0 (5.0, 6.0) | 4.0 (2.0, 5.0) | 7.5 (6.3, 8.0) | 5.0 (4.3, 5.8) | 0.004 |

Example 5—In Vivo Effect of AMH Receptor Binding Peptides on Tissue Markers, Serum Hormones, and Cell Proliferation/Apoptosis This example describes the effect of the AMH receptor binding peptide AMHR2BP (SEQ ID NO: 1) on the expression of various tissue markers and serum hormones in vivo. This example also describes the effect of AMHR2BP (SEQ ID NO: 1) on cellular proliferation and apoptosis in vivo. Briefly, mice were treated and harvested as described in Example 4. That is, ovarian cortex specimens from Example 4 were flash-frozen and subsequently stored with the mouse's study identification number in liquid nitrogen until ready for future real-time RT-PCR analysis. Mouse serum samples were also cryopreserved for future analysis.

RT-PCR

RT-PCR is performed according to the methods described in Example 3. More particularly, RT-PCR is used to assess ovarian tissue expression of AMH-R2, FSH-R, LH receptor, AMH, and inhibin-B mRNA levels in the four groups of mice from Example 4. RT-PCR is also used to determine mRNA levels of Ki67 (cell proliferation marker) and Caspase 3 (cell apoptosis marker). In the AMHR2BP (SEQ ID NO: 1) group, cellular mRNA expression of AMH, AMH-R2, FSH-R, Inhibin B, Ki67, and Caspase is reduced relative to the mRNA expression of these markers in the baseline group and control group. Cellular mRNA expression of the LH receptor is unchanged or decreases slightly. Further, and with taking into account dose-effect differences, the AMHR2BP (SEQ ID NO: 1) group and rAMH group are similar in cellular mRNA expression of AMH, AMH-R2, FSH-R, Inhibin B, Ki67, Caspase, and LH receptor.

Serum Markers

Mouse serum from the mouse groups identified in Example 4 are analyzed for estradiol, progesterone, AMH, FSH, LH, and Inhibin B. In the AMHR2BP (SEQ ID NO: 1) group, serum estradiol is unchanged as compared to the control and baseline groups, progesterone is similar, or lower than control and baseline groups, AMH is similar to the control and baseline groups (or slightly lower), FSH and LH are unchanged versus the control and baseline groups, while Inhibin B is unchanged, or increased relative to the control and baseline groups. Further, and with taking into account dose-effect differences, the AMHR2BP (SEQ ID NO: 1) group and rAMH group show similar levels of serum estradiol, progesterone, AMH, FSH, LH, and Inhibin B.

Cell Proliferation

Cell proliferation and apoptosis assays are performed using the TACS MTT Cell Proliferation Assay (Trevigen™, Gaithersburg, Md.). In the AMHR2BP (SEQ ID NO: 1) group, granulosa cells exhibit a lower proliferation rate and lower apoptosis rate compared to baseline and control groups. Further, and with taking into account dose-effect differences, the AMHR2BP (SEQ ID NO: 1) group and rAMH group show similar proliferation and apoptosis profiles.

REFERENCES

Each of the following references are expressly incorporated herein in their entirety:

1. Durlinger A L L, Kramer P, Karels B, et al. Control of primordial follicle recruitment by anti-Mullerian hormone in the mouse ovary. Endocrinol 1999; 140:5789-96.
2. Di Clemente N, Goxe B, Remy J J, et al. Inhibitory effect of AMH upon aromatase activity and LH receptors of granulosa cells of rat and porcine immature ovaries. Endocrine 1994; 2:553-8.
3. Durlinger A L L, Visser J A, Themmen A P N. Regulation of ovarian function: the role of anti-Mullerian hormone. Reprod 2002; 124:601-9.
4. Kevenaar M E, Meerasahib M F, Kramer P, et al. Serum anti-mullerian hormone levels reflect the size of the primordial follicle pool in mice. Endocrinol 2006; 147: 3228-34.
5. Visser J A, de Jong F H, Laven J S, Themmen A P. Anti-Mullerian hormone: a new marker for ovarian function. Reprod 2006; 131: 1-9.
6. de Vet A, Laven J S, de Jong F H, Themmen A P N, Fauser B C. Antimullerian hormone serum levels: a putative marker for ovarian aging. Fertil Steril 2002; 77:357-62.
7. Fanchin R, Schonauer L M, Righini C, Guibourdenche J, Frydman R, Taieb J. Serum anti-Mullerian hormone is more strongly related to ovarian follicular status than serum inhibin B, estradiol, FSH and LH on day 3. Hum Reprod 2003; 18:323-7.
8. Detti L, Fletcher N M, Saed G M, Peregrin-Alvarez I, Uhlmann R A. Anti-Mullerian Hormone (AMH) may stall ovarian cortex function through modulation of hormone receptors other than the AMH receptor. Reprod Sci 2018; 25(8):1218-1223.
9. Detti L, Fletcher N M, Saed G M, Sweatman T, Uhlmann R A, Pappo A, Peregrin-Alvarez I. Xenotransplantation of pre-pubertal ovarian cortex and prevention of follicle depletion with anti-Müllerian hormone (AMH). J Assist Reprod Genet 2018; 35:1831-1841. Doi: 10.1007/s10815-018-1260-z.
10. Detti L, Harper A K, Fan R, Peregrin-Alvarez I, Roman R A, Levi D'Ancona R, Morris R T, Saed G M. The Loss of Response to the Inhibitory Action of Anti-Müllerian Hormone (AMH) through Downregulation of its Receptor is a Potential Mechanism of Chemoresistance in Ovarian Cancer Cells. Society for Reproductive Investigation Annual Meeting, Mar. 12-16, 2019, Paris, France.

11. Detti L, Fletcher N M, Uhlmann R A, Peregrin-Alvarez I, Roman R A, Saed G M. Anti-Mullerian Hormone (AMH) regulates ovarian cortex's sternness potential in fresh and vitrified/thawed ovarian cortex. Minerva Ginecologica, 2019; 71:249-253. doi: 10.23736/S0026-4784.
12. Kano M, Sosulski A E, Zhang L, Saatcioglu H D, Wang D, Nagykery N, Sabatini M E, Gao G, Donahoe P K, Pepin D. AMH/MIS as a contraceptive that protects the ovarian reserve during chemotherapy. Proc Natl Acad Sci USA 2017 Feb. 28; 114(9): E1688-E169'1.
13. Kim D, Suh E. Defying DNA double-strand break-induced death during prophase I meiosis by temporal Tap63a phosphorylation regulation in developing mouse oocytes. Mol Cell Biol 2014; 34:1460-1473.
14. Parry R L, Chin T W, Epstein J, Hudson P L, Powell D M, Donahoe P K. Recombinant human 50ullerian inhibiting substance inhibits human ocular melanoma cell lines in vitro and in vivo. Canc. Res 1992; 52:1182-6.
15. Detti L, Christiansen M E, Francillon L, Ikwuezunma G, Mari G, Tobiasz A M. Anti-Müllerian hormone (AMH) profiles in mothers with polycystic ovary syndrome (PCOS) and their term fetuses. Syst Biol Reprod Med 2019; 65:147-54.
16. Norwick N, Osborne S E, Carter C, Williams L J, Uhlmann R A, Detti L. Anti-mullerian hormone (AMH) serum measurements reflect cycle length and ovarian follicle number in women with polycystic ovary syndrome (PCOS). Obstet Gynecol 2015; 125:110S.
17. Andersen J M, Herning H, Witczak O, Haugen T B. Anti-Müllerian hormone in seminal plasma and serum: association with sperm count and sperm motility. Hum Reprod 2016 August; 31(8):1662-7.
18. Nery S F, Vieira M A, Dela Cruz C, Lobach V N, Del Puerto H L, Torres P B, Rocha A L, Reis A B, Reis F M. Seminal plasma concentrations of Anti-Mullerian hormone and inhibin B predict motile sperm recovery from cryopreserved semen in asthenozoospermic men: a prospective cohort study. Andrology 2014; 6:918-923.
19. Durlinger A L, Gruijters M J, Kramer P, Karels B, Kumar T R, Matzuk M M, et al. Anti-Müllerian hormone attenuates the effects of FSH on follicle development in the mouse ovary. Endocrinology 2001; 142:4891-9.
20. Josso N, di Clemente N, Gouedard L. Anti-Mullerian hormone and its receptors. Mol Cell Endocrinol. 2001; 179:25-32.
21. Ratteralli J L, Levi A J, Miller B T. A prospective novel method of determining ovarian size during in vitro fertilization cycles. J Assist Reprod Genet 2002; 19:39-41.
22. Ingraham H A, Hirokawa Y, Roberts L M, Mellon S H, McGee E, Nachtigal M W, et al. Autocrine and paracrine mullerian inhibiting substance hormone signaling in reproduction. Recent Prog Horm Res 2000; 55:53-67.
23. Pellat L, Rice S, Dilaver N, Heshri A, Galea R, Brincat M, Brown K, Simpson E R, Mason H D. Anti-Müllerian hormone reduces follicle sensitivity to follicle-stimulating hormone in human granulosa cells. Fertil Steril 2011; 96:1246-51.
24. Detti L, Fletcher N M, Saed G M, Peregrin-Alvarez I, Uhlmann R A. Anti-Müllerian Hormone (AMH) may stall ovarian cortex function through modulation of hormone receptors other than the AMH receptor. Reprod Sci 2018; 25(8):1218-1223. doi: 10.1177/1933719117737850.
25. Hu R, Wang F M, Yu L, Luo Y, Wu X, Li J, Zhang X M, Oehninger S, Bocca S. Antimüllerian hormone regulates stem cell factor expression in human granulosa cells. Fertil Steril. 2014; 102:1742-50.e1.
26. Detti L, Abuzeid M I, Peregrin-Alvarez I, Christiansen M E, Malekzadeh P, Sledge J, Saed G M. Recombinant anti-Müllerian hormone (rAMH) for stalling in vitro granulosa cell replication. Accepted 2020. Reproductive Sciences.
27. Detti L, Uhlmann R A, Lu M, Zhang J, Saed G M, Fletcher N M, Diamond M P, Williams J L. Goserelin fosters bone elongation, but does not prevent ovarian damage, in cyclophosphamide-treated pre-pubertal mice. Fertil Steril 2014; 101:1157-1164.
28. Hayes E, Kushnir V, Ma X, et al. Intra-cellular mechanism of anti-Müllerian hormone (AMH) in regulation of follicular development. Mol Cell Endocrinol. 2016; 433: 56-65.
29. Roness H, Spector I, Leichtmann-Bardoogo Y, Savino A M, Dereh-Haim S, Meirow D. Pharmacological administration of recombinant human AMH rescues ovarian reserve and preserves fertility in a mouse model of chemotherapy, without interfering with anti-tumoural effects. J Assist Reprod Genet. 2019 September; 36(9): 1793-1803.
30. Kushnir V A, Seifer D B, Barad D H, et al. Potential therapeutic applications of human anti-Müllerian hormone (AMH) analogues in reproductive medicine. J Assist Reprod Genet. 2017 Jun. 22. doi: 10.1007/s10815-017-0977-4.
31. Melchionna M, Styian K E, Marches an S. The Unexpected Advantages of Using D-Amino Acids for Peptide Self-Assembly into Nanostructured Hydrogels for Medicine. Curr Top Med Chem 2016; 16(18):2009-18.
32. Detti L, Abuzeid M I, Peregrin-Alvarez I, Christiansen M E, Malekzadeh P, Sledge J, Saed G M. Recombinant anti-Müllerian hormone (rAMH) for stalling in vitro granulosa cell replication. In Press, Reproductive Sciences, 2020.

What is claimed is:

1. An anti-Mullerian hormone receptor 2 (AMH-R$_2$) binding peptide or functional fragment thereof, the AMH-R2 binding peptide or functional fragment thereof comprising any one of the amino acid sequences set forth as SEQ ID NOS: 1-20, wherein each of the amino acid sequences set forth as SEQ ID NOS: 1-20 optionally comprises a single amino acid substitution.

2. The AMH-R$_2$ binding peptide or functional fragment thereof of claim 1, wherein the amino acid sequence set forth as any one of SEQ ID NOS: 1-20 and optionally comprising the single amino acid substitution further comprises at least one D-form amino acid.

3. The AMH-R$_2$ binding peptide or functional fragment thereof of claim 1, wherein the AMH-R$_2$ binding peptide or fragment thereof is an AMH-R$_2$ agonist.

4. A method for activating an anti-Mullerian hormone receptor 2 (AMH-R$_2$) in a subject, the method comprising administering to the subject an effective amount of the AMH-R$_2$ binding peptide or functional fragment thereof of claim 1.

5. The method of claim 4, wherein the administration of the AMH-R$_2$ binding peptide or functional fragment thereof inhibits ovarian follicle development in the subject.

6. The method of claim 4, wherein administration of the AMH-R$_2$ binding peptide or functional fragment thereof delays menopause in the subject.

7. The method of claim 6, wherein the menopause is natural menopause or iatrogenic menopause.

8. The method of claim 4, further comprising administering estrogen or progesterone or a combination thereof to the subject.

9. A composition for use in stimulating an Anti-Mullerian Hormone receptor 2 (AMH-R$_2$), the composition comprising an AMH-R$_2$ binding peptide or functional fragment thereof, the AMH-R$_2$ binding peptide or functional fragment thereof comprising any one of the amino acid sequences set forth as SEQ ID NOS: 1-20, wherein each of the amino acid sequences set forth as SEQ ID NOS: 1-20 optionally comprises a single amino acid substitution.

10. The composition of claim 9, wherein the composition further comprises a pharmaceutically acceptable carrier.

11. A method of modulating folliculogenesis in a subject, the method comprising administering an effective amount an anti-Mullerian hormone receptor 2 (AMH-R$_2$) binding peptide or functional fragment thereof to the subject, the AMH-R$_2$ binding peptide or functional fragment thereof comprising any one of the amino acid sequences set forth as SEQ ID NOS: 1-20, wherein each of the amino acid sequences set forth as SEQ ID NOS: 1-20 optionally comprises a single amino acid substitution.

12. A method of inhibiting premature follicle activation in a subject, the method comprising administering to the subject a therapeutically effective amount of a pharmaceutical composition comprising an anti-Mullerian hormone receptor 2 (AMH-R$_2$) binding peptide or functional fragment thereof, the AMH-R$_2$ binding peptide or functional fragment thereof comprising any one of the amino acid sequences set forth SEQ ID NOS: 1-20, wherein each of the amino acid sequences set forth as SEQ ID NOS: 1-20 optionally comprises a single amino acid substitution.

13. The AMH-R$_2$ binding peptide or functional fragment thereof of claim 1, wherein the AMH-R$_2$ binding peptide comprises the amino acid sequence set forth as SEQ ID NO: 1 or SEQ ID NO: 2, the amino acid sequence optionally comprising a single amino acid substitution.

14. The AMH-R$_2$ binding peptide or functional fragment thereof of claim 1, wherein the AMH-R$_2$ binding peptide or functional fragment thereof comprises the amino acid sequence set forth as any one of SEQ ID NOS: 1-20.

15. The AMH-R$_2$ binding peptide or functional fragment thereof of claim 14, wherein the AMH-R$_2$ binding peptide or functional fragment thereof comprises the amino acid sequence set forth as SEQ ID NO: 1 or SEQ ID NO: 2.

16. The method of claim 4, wherein administering the AMH-R$_2$ binding peptide or functional fragment thereof preserves ovarian follicle reserves in the subject and wherein the subject is a cancer patient.

17. The composition of claim 9, wherein (i) the AMH-R$_2$ binding peptide or functional fragment thereof comprises the amino acid sequence set forth as SEQ ID NO: 1 or SEQ ID NO: 2 and wherein (ii) each of the amino acid sequences set forth as SEQ ID NO: 1 or SEQ ID NO: 2 comprises at least one D-form amino acid and optionally at least one amino acid substitution.

18. The composition of claim 9, wherein the composition further comprises estrogen or progesterone or a combination thereof.

19. The method of claim 11, wherein (i) the AMH-R$_2$ binding peptide or functional fragment thereof comprises the amino acid sequence set forth as SEQ ID NO: 1 or SEQ ID NO: 2 and wherein (ii) each of the amino acid sequences set forth as SEQ ID NO: 1 or SEQ ID NO: 2 comprises at least one D-form amino acid and optionally at least one amino acid substitution.

20. The method of claim 12, wherein (i) the AMH-R$_2$ binding peptide or functional fragment thereof comprises the amino acid sequence set forth as SEQ ID NO: 1 or SEQ ID NO: 2 and wherein (ii) each of the amino acid sequences set forth as SEQ ID NO: 1 or SEQ ID NO: 2 comprises at least one D-form amino acid and optionally at least one amino acid substitution.

* * * * *

SEQUENCE LISTING

<160> NUMBER OF SEQ ID NOS: 34

<210> SEQ ID NO 1
<211> LENGTH: 17
<212> TYPE: PRT
<213> ORGANISM: Artificial Sequence
<220> FEATURE:
<223> OTHER INFORMATION: Synthetic AMH receptor binding peptide

<400> SEQUENCE: 1

Val Gly Ser Asn Ala Tyr Asn Gln Phe Arg Val Ser Gly Val Ala Leu
1               5                   10                  15

Ser

<210> SEQ ID NO 2
<211> LENGTH: 15
<212> TYPE: PRT
<213> ORGANISM: Artificial Sequence
<220> FEATURE:
<223> OTHER INFORMATION: Synthetic AMH receptor binding peptide

<400> SEQUENCE: 2

Asn Gly Ser Ser Leu Gln Ala Val Asn Arg Leu Ser Gly Val Ser
1               5                   10                  15

<210> SEQ ID NO 3
<211> LENGTH: 17
<212> TYPE: PRT
<213> ORGANISM: Artificial Sequence
<220> FEATURE:
<223> OTHER INFORMATION: Synthetic AMH receptor binding peptide

<400> SEQUENCE: 3

Tyr Trp Gly Trp Ser His Ala Lys Ala Asn Gln Phe Pro Asn Arg Leu
1               5                   10                  15

Ala

<210> SEQ ID NO 4
<211> LENGTH: 17
<212> TYPE: PRT
<213> ORGANISM: Artificial Sequence
<220> FEATURE:
<223> OTHER INFORMATION: Synthetic AMH receptor binding peptide

<400> SEQUENCE: 4

Arg Trp Gly Ala Ser Asn Lys His Phe Ala Asn Ala Asn Gln Arg Ala
1               5                   10                  15

Leu

<210> SEQ ID NO 5
<211> LENGTH: 17
<212> TYPE: PRT
<213> ORGANISM: Artificial Sequence
<220> FEATURE:
<223> OTHER INFORMATION: Synthetic AMH receptor binding peptide

<400> SEQUENCE: 5

Asp Gly Leu Gly Ser Val Leu Ala Arg Lys Asn Arg Arg Asp Ala Val
1               5                   10                  15

Leu

<210> SEQ ID NO 6
<211> LENGTH: 17
<212> TYPE: PRT
<213> ORGANISM: Artificial Sequence
<220> FEATURE:
<223> OTHER INFORMATION: Synthetic AMH receptor binding peptide

<400> SEQUENCE: 6

Val Gly Pro Ser Val Ala Tyr Asn Tyr Arg Val Ser Gly Val Ala Leu
1               5                   10                  15

Gly

<210> SEQ ID NO 7
<211> LENGTH: 17
<212> TYPE: PRT

```
<213> ORGANISM: Artificial Sequence
<220> FEATURE:
<223> OTHER INFORMATION: Synthetic AMH receptor binding peptide

<400> SEQUENCE: 7

Lys Gly Gly Tyr Ser Asn Ala Tyr Lys His Asn Pro Arg Val Leu Gly
1               5                   10                  15

Ser

<210> SEQ ID NO 8
<211> LENGTH: 17
<212> TYPE: PRT
<213> ORGANISM: Artificial Sequence
<220> FEATURE:
<223> OTHER INFORMATION: Synthetic AMH receptor binding peptide

<400> SEQUENCE: 8

Trp His Gly Trp Ser Gly Ala Asn Leu Phe Pro Tyr Arg Ser Gly Val
1               5                   10                  15

Ser

<210> SEQ ID NO 9
<211> LENGTH: 17
<212> TYPE: PRT
<213> ORGANISM: Artificial Sequence
<220> FEATURE:
<223> OTHER INFORMATION: Synthetic AMH receptor binding peptide

<400> SEQUENCE: 9

Val Gly Trp Ser Phe Ala Pro Asn Gly Tyr Arg Leu Ser Gly Val Leu
1               5                   10                  15

Gly

<210> SEQ ID NO 10
<211> LENGTH: 17
<212> TYPE: PRT
<213> ORGANISM: Artificial Sequence
<220> FEATURE:
<223> OTHER INFORMATION: Synthetic AMH receptor binding peptide

<400> SEQUENCE: 10

Arg Gly Arg Ser Gln Ala Tyr Asn Glu Arg Ser Gly Val Ala Leu Ser
1               5                   10                  15

Gly

<210> SEQ ID NO 11
<211> LENGTH: 17
<212> TYPE: PRT
<213> ORGANISM: Artificial Sequence
<220> FEATURE:
<223> OTHER INFORMATION: Synthetic AMH receptor binding peptide

<400> SEQUENCE: 11

Gly Ser Trp Ser Gly Ala His Asn Phe Arg Lys Ser Gly Val Leu Ser
1               5                   10                  15

Gly

<210> SEQ ID NO 12
<211> LENGTH: 17
<212> TYPE: PRT
<213> ORGANISM: Artificial Sequence
<220> FEATURE:
<223> OTHER INFORMATION: Synthetic AMH receptor binding peptide
```

```
<400> SEQUENCE: 12

Gly Leu Gln Trp Ser Phe Ala Asn Gly Gln Trp Arg Gly Ala Leu Ser
1               5                   10                  15

Gly

<210> SEQ ID NO 13
<211> LENGTH: 17
<212> TYPE: PRT
<213> ORGANISM: Artificial Sequence
<220> FEATURE:
<223> OTHER INFORMATION: Synthetic AMH receptor binding peptide

<400> SEQUENCE: 13

Arg Gly Ser Tyr Ser Asn Leu Phe Ala Asn Ser Gly Glu Arg Val Gly
1               5                   10                  15

Val

<210> SEQ ID NO 14
<211> LENGTH: 17
<212> TYPE: PRT
<213> ORGANISM: Artificial Sequence
<220> FEATURE:
<223> OTHER INFORMATION: Synthetic AMH receptor binding peptide

<400> SEQUENCE: 14

Phe Asn Gly Pro Ser Ala Arg Asn Phe Tyr Arg His Asp Val Ala Val
1               5                   10                  15

Ser

<210> SEQ ID NO 15
<211> LENGTH: 17
<212> TYPE: PRT
<213> ORGANISM: Artificial Sequence
<220> FEATURE:
<223> OTHER INFORMATION: Synthetic AMH receptor binding peptide

<400> SEQUENCE: 15

Asn Gly Arg Ser Gln Ala His Asn Leu Arg Lys Ala Gly Val Ala Leu
1               5                   10                  15

Ser

<210> SEQ ID NO 16
<211> LENGTH: 17
<212> TYPE: PRT
<213> ORGANISM: Artificial Sequence
<220> FEATURE:
<223> OTHER INFORMATION: Synthetic AMH receptor binding peptide

<400> SEQUENCE: 16

Tyr Gly Phe Pro Ser Ala Arg Val Asn Arg Tyr Trp Asn Arg His Asp
1               5                   10                  15

Ala

<210> SEQ ID NO 17
<211> LENGTH: 17
<212> TYPE: PRT
<213> ORGANISM: Artificial Sequence
<220> FEATURE:
<223> OTHER INFORMATION: Synthetic AMH receptor binding peptide

<400> SEQUENCE: 17

Glu Gly Leu Gln Ser Ser Ala Tyr Asn Asn Tyr Trp Arg Lys Leu Val
1               5                   10                  15
```

Ala

<210> SEQ ID NO 18
<211> LENGTH: 17
<212> TYPE: PRT
<213> ORGANISM: Artificial Sequence
<220> FEATURE:
<223> OTHER INFORMATION: Synthetic AMH receptor binding peptide

<400> SEQUENCE: 18

Gly Leu Tyr Trp Ser Ala Tyr Asn Pro Trp Arg His Val Ala Leu Ala
1               5                   10                  15

Ser

<210> SEQ ID NO 19
<211> LENGTH: 17
<212> TYPE: PRT
<213> ORGANISM: Artificial Sequence
<220> FEATURE:
<223> OTHER INFORMATION: Synthetic AMH receptor binding peptide

<400> SEQUENCE: 19

Gly Gly Arg Ser Val Ser Ala Asn Leu Gln Arg Glu Arg Lys Val Ala
1               5                   10                  15

Gly

<210> SEQ ID NO 20
<211> LENGTH: 17
<212> TYPE: PRT
<213> ORGANISM: Artificial Sequence
<220> FEATURE:
<223> OTHER INFORMATION: Synthetic AMH receptor binding peptide

<400> SEQUENCE: 20

Lys Gly Ser Asn Ala Arg Lys Asn Arg Arg Asp Ala Ser Gly Val Ala
1               5                   10                  15

Leu

<210> SEQ ID NO 21
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 21
cacattgcgt tgattcagta                                           20

<210> SEQ ID NO 22
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 22
aataaagcca tgccaatctc                                           20

<210> SEQ ID NO 23
<211> LENGTH: 18
<212> TYPE: DNA
<213> ORGANISM: Artificial Sequence
<220> FEATURE:
<223> OTHER INFORMATION: Synthetic oligonucleotide

```
<400> SEQUENCE: 23
gtagaagtcg tcgtcgtg                                                    18

<210> SEQ ID NO 24
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 24
ctccgacagg ctgatgag                                                    18

<210> SEQ ID NO 25
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 25
gacagtcggc acgaagacc                                                   19

<210> SEQ ID NO 26
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 26
tggaaagggg tggctctct                                                   19

<210> SEQ ID NO 27
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 27
actaccttcc tcatacaga                                                   19

<210> SEQ ID NO 28
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 28
atcactgtaa cttgctaatc a                                                21

<210> SEQ ID NO 29
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 29
gtccagaatc cacgggtggt ttcct                                            25

<210> SEQ ID NO 30
```

```
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 30
tgatggttga ggctgttcct tgatg                                              25

<210> SEQ ID NO 31
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 31
ggaacctacc cacaacacct g                                                  21

<210> SEQ ID NO 32
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 32
gggctaaatg acttagaggg acaa                                               24

<210> SEQ ID NO 33
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 33
gcatcccgtc ctcaaagtcc                                                    20

<210> SEQ ID NO 34
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 34
ccaccatgtt ccacctgtca                                                    20
```